(12) United States Patent
Heidecke et al.

(10) Patent No.: US 10,191,058 B2
(45) Date of Patent: Jan. 29, 2019

(54) DIAGNOSIS OF CANCER BY DETECTING AUTO-ANTIBODIES AGAINST VASCULAR ENDOTHELIAL GROWTH FACTOR RECEPTOR (VEGFR)

(71) Applicant: CELLTREND GMBH, Luckenwalde (DE)

(72) Inventors: Harald Heidecke, Berlin (DE); Kai Schulze-Forster, Teltow (DE)

(73) Assignee: CELLTREND GMBH, Luckenwalde (DE)

( * ) Notice: Subject to any disclaimer, the term of this patent is extended or adjusted under 35 U.S.C. 154(b) by 0 days.

(21) Appl. No.: 15/115,904

(22) PCT Filed: Feb. 3, 2015

(86) PCT No.: PCT/EP2015/052188
§ 371 (c)(1),
(2) Date: Aug. 1, 2016

(87) PCT Pub. No.: WO2015/117955
PCT Pub. Date: Aug. 13, 2015

(65) Prior Publication Data
US 2017/0176444 A1    Jun. 22, 2017

(30) Foreign Application Priority Data
Feb. 4, 2014 (EP) .................................... 14153825

(51) Int. Cl.
| | | |
|---|---|---|
| *A61K 39/00* | (2006.01) | |
| *G01N 33/574* | (2006.01) | |
| *G01N 33/564* | (2006.01) | |
| *G01N 33/74* | (2006.01) | |
| *C07K 14/71* | (2006.01) | |
| *C07K 16/28* | (2006.01) | |
| *A61K 39/395* | (2006.01) | |

(52) U.S. Cl.
CPC ... *G01N 33/57449* (2013.01); *A61K 39/3955* (2013.01); *C07K 14/71* (2013.01); *C07K 16/2863* (2013.01); *G01N 33/564* (2013.01); *G01N 33/74* (2013.01); *C07K 2317/24* (2013.01); *G01N 2333/475* (2013.01)

(58) Field of Classification Search
CPC .... G01N 33/53; G01N 33/543; G01N 33/566; G01N 33/574; G01N 33/57484; G01N 33/57488; G01N 33/577; G01N 33/588
See application file for complete search history.

(56) References Cited

U.S. PATENT DOCUMENTS

| 2008/0254481 A1 | 10/2008 | Love et al. |
| 2009/0075299 A1 | 3/2009 | Mathew et al. |

FOREIGN PATENT DOCUMENTS

| CN | 104356226 A | 2/2015 |
| WO | 2005043165 A2 | 5/2005 |
| WO | 2009055382 A2 | 4/2009 |
| WO | 2012139052 A2 | 10/2012 |

OTHER PUBLICATIONS

Ren, S., et al., Vaccine, 29: 5802-5811, 2011.*
Barua, A., et al. Abstract 2455: "Molecular targeted imaging of vascular endothelial growth factor receptor (VEGFR)-2 and anti-NMP autoantibodies detect ovarian tumor at early stage", Cancer Research, Proceedings AACR 103rd Annual Meeting Mar. 31, 2012-Apr. 4, 2012, Chicago, IL.*
International Search Report dated Apr. 21 2015, issued in PCT/EP2015/052188.
Liu et al., "Immunotherapy of tumors with vaccine based on quail homologous vascular endothelial growth factor receptor-2" Blood. (Sep. 1, 2003) vol. 103, No. 5: 1815-1823.

* cited by examiner

*Primary Examiner* — Lei Yao
(74) *Attorney, Agent, or Firm* — McBee Moore Woodward & Vanik IP, LLC; Susan McBee; Chester Moore

(57) ABSTRACT

The present invention relates to a method for diagnosis of a cancer, comprising the steps of (i) determining the level of antibodies against vascular endothelial growth factor receptor (VEGFR) in a sample from a subject to be diagnosed, (ii) comparing the determined level in the sample to a control level derived from subjects without cancer; wherein a decreased level in the sample from the subject to be diagnosed as compared to the control level is indicative for cancer in the subject. Furthermore, the invention relates to method of predicting response and outcome of a treatment of a cancer with an angiogenesis inhibitor.

14 Claims, 11 Drawing Sheets
Specification includes a Sequence Listing.

A

B

A

B

C

SEQUENCE LISTING

<160> NUMBER OF SEQ ID NOS: 2

<210> SEQ ID NO 1
<211> LENGTH: 687
<212> TYPE: PRT
<213> ORGANISM: Homo sapiens
<220> FEATURE:
<221> NAME/KEY: MISC_FEATURE
<222> LOCATION: (1)..(687)
<223> OTHER INFORMATION: Amino acid sequence of sVEGFR-1 (sFlt1)

<400> SEQUENCE: 1

```
Met Val Ser Tyr Trp Asp Thr Gly Val Leu Leu Cys Ala Leu Leu Ser
1               5                   10                  15

Cys Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
                35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350
```

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685

<210> SEQ ID NO 2
<211> LENGTH: 1338
<212> TYPE: PRT
<213> ORGANISM: Homo sapiens
<220> FEATURE:
<221> NAME/KEY: MISC_FEATURE
<222> LOCATION: (1)..(1338)
<223> OTHER INFORMATION: Amino acid sequence of mbVEGFR-1 (isoform 1)

<400> SEQUENCE: 2

Met Val Ser Tyr Trp Asp Thr Gly Val Leu Leu Cys Ala Leu Leu Ser
1               5                   10                  15

```
Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
        290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
            370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
```

```
                435                 440                 445
Arg Gln Ile Leu Thr Cys Thr Ala Tyr Gly Ile Pro Gln Pro Thr Ile
450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                    485                 490                 495
Asn Met Gly Asn Arg Ile Glu Ser Ile Thr Gln Arg Met Ala Ile Ile
                500                 505                 510
Glu Gly Lys Asn Lys Met Ala Ser Thr Leu Val Val Ala Asp Ser Arg
            515                 520                 525
Ile Ser Gly Ile Tyr Ile Cys Ile Ala Ser Asn Lys Val Gly Thr Val
            530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                    565                 570                 575
Cys Thr Val Asn Lys Phe Leu Tyr Arg Asp Val Thr Trp Ile Leu Leu
                580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                    645                 650                 655
Asp Gln Glu Ala Pro Tyr Leu Leu Arg Asn Leu Ser Asp His Thr Val
                660                 665                 670
Ala Ile Ser Ser Ser Thr Thr Leu Asp Cys His Ala Asn Gly Val Pro
            675                 680                 685
Glu Pro Gln Ile Thr Trp Phe Lys Asn Asn His Lys Ile Gln Gln Glu
            690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                    725                 730                 735
Lys Gly Ser Val Glu Ser Ser Ala Tyr Leu Thr Val Gln Gly Thr Ser
                740                 745                 750
Asp Lys Ser Asn Leu Glu Leu Ile Thr Leu Thr Cys Thr Cys Val Ala
            755                 760                 765
Ala Thr Leu Phe Trp Leu Leu Leu Thr Leu Phe Ile Arg Lys Met Lys
            770                 775                 780
Arg Ser Ser Ser Glu Ile Lys Thr Asp Tyr Leu Ser Ile Ile Met Asp
785                 790                 795                 800
Pro Asp Glu Val Pro Leu Asp Glu Gln Cys Glu Arg Leu Pro Tyr Asp
                    805                 810                 815
Ala Ser Lys Trp Glu Phe Ala Arg Glu Arg Leu Lys Leu Gly Lys Ser
                820                 825                 830
Leu Gly Arg Gly Ala Phe Gly Lys Val Val Gln Ala Ser Ala Phe Gly
            835                 840                 845
Ile Lys Lys Ser Pro Thr Cys Arg Thr Val Ala Val Lys Met Leu Lys
            850                 855                 860
```

```
Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
                900                 905                 910

Lys Tyr Gly Asn Leu Ser Asn Tyr Leu Lys Ser Lys Arg Asp Leu Phe
                915                 920                 925

Phe Leu Asn Lys Asp Ala Ala Leu His Met Glu Pro Lys Lys Glu Lys
930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
                980                 985                 990

Pro Ile Thr Met Glu Asp Leu Ile Ser Tyr Ser Phe Gln Val Ala Arg
                995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260
```

-continued

| | | | | | | | | | | | | | | |
|---|---|---|---|---|---|---|---|---|---|---|---|---|---|---|
| Lys | Pro 1265 | Lys | Ala | Ser | Leu 1270 | Lys | Ile | Asp | Leu | Arg 1275 | Val | Thr | Ser | Lys |
| Ser | Lys 1280 | Glu | Ser | Gly | Leu 1285 | Ser | Asp | Val | Ser | Arg 1290 | Pro | Ser | Phe | Cys |
| His | Ser 1295 | Ser | Cys | Gly | His 1300 | Val | Ser | Glu | Gly | Lys 1305 | Arg | Arg | Phe | Thr |
| Tyr | Asp 1310 | His | Ala | Glu | Leu 1315 | Glu | Arg | Lys | Ile | Ala 1320 | Cys | Cys | Ser | Pro |
| Pro | Pro 1325 | Asp | Tyr | Asn | Ser 1330 | Val | Val | Leu | Tyr | Ser 1335 | Thr | Pro | Pro | Ile |

DIAGNOSIS OF CANCER BY DETECTING AUTO-ANTIBODIES AGAINST VASCULAR ENDOTHELIAL GROWTH FACTOR RECEPTOR (VEGFR)

CROSS REFERENCE TO RELATED APPLICATIONS

This application is a § 371 National Stage Application of PCT/EP2015/052188, filed 3 Feb. 2015, which claims priority to EP 14153825.6, filed 4 Feb. 2014.

FIELD OF THE INVENTION

The present invention is in the field of diagnostics, prognosis and therapeutics for cancer, more in particular in the field of diagnosis and therapy of VEGF or VEGFR associated cancer, more particular in the field of diagnosis, prognosis and therapy of ovarian cancer.

BACKGROUND OF THE INVENTION

According to the American Cancer Society ovarian cancer is expected to account for over 22,000 new cancer diagnoses and more than 14,000 deaths in 2013 in the US alone. Of the gynaecologic malignancies, ovarian cancer has the highest mortality rate. In early stages of the disease, ovarian cancer is nearly asymptomatic. Hence, a large portion of the patients present with clinically advanced stages of ovarian cancer. However, the 5-year survival rate for patients diagnosed with early-stage disease is often >90%, but it is <20% for advanced-stage disease, underscoring the importance of early detection.

Current diagnosis of ovarian cancer relies on pelvic exam, transvaginal ultrasonography, (TVS), abdominal ultrasonography, and exploratory or diagnostic laparoscopy. The most commonly used biomarker for clinical screening and prognosis in patients with ovarian cancer is ovarian cancer antigen 125 (CA125) (Coticchia et al. (2008), J. Natl. Compr. Canc. Netw. 6(8):795-802). Serum CA125 levels are elevated in ≈80% of patients with advanced-stage epithelial ovarian cancer but are increased in only 50-60% of patients with early-stage disease. Serum CA125 levels may be falsely elevated in women with any i.p. pathology resulting in irritation of the serosa of the peritoneum or pericardium, uterine fibroids, renal disorders, and normal menses. Moreover, serum CA125 levels do not predict the outcome of cytoreductive surgery in patients with advanced epithelial ovarian cancer. Further biomarkers include, for example, Human Epidymis Protein 4 (HE4) and Mesothelin (Sarojini et al. (2012), Journal of Oncology 102, Article ID 709049). Severeness of ovarian cancer is categorized by the grade and stage of tumorization. This nowadays can only be performed by evaluation of the tumors under or after surgical treatment or by combining marker evaluation and (histological) evaluation of tissue. Staging is very important because ovarian cancers have different prognosis at different stages and may be treated differently. The accuracy of the staging may determine whether or not a patient will be cured. If the cancer isn't accurately staged, then cancer that has spread outside the ovary might be missed and not treated. Once a stage has been given it does not change, even when the cancer comes back or spreads to new locations in the body.

Ovarian cancer staging is by FIGO staging system uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary tumor (T), the absence or presence of metastasis to nearby lymph Nodes (N), and the absence or presence of distant Metastasis (M).

| | |
|---|---|
| Stage I | limited to one or both ovaries |
| IA | involves one ovary; capsule intact; no tumor on ovarian surface; no malignant cells in ascites or peritoneal washings |
| IB | involves both ovaries; capsule intact; no tumor on ovarian surface; negative washings |
| IC | tumor limited to ovaries with any of the following: capsule ruptured, tumor on ovarian surface, positive washings |
| Stage II | pelvic extension or implants |
| IIA | extension or implants onto uterus or fallopian tube; negative washings |
| IIB | extension or implants onto other pelvic structures; negative washings |
| IIC | pelvic extension or implants with positive peritoneal washings |
| Stage III | peritoneal implants outside of the pelvis; or limited to the pelvis with extension to the small bowel or omentum |
| IIIA | microscopic peritoneal metastases beyond pelvis |
| IIIB | macroscopic peritoneal metastases beyond pelvis less than 2 cm in size |
| IIIC | peritoneal metastases beyond pelvis >2 cm or lymph node metastases |
| Stage IV | distant metastases to the liver or outside the peritoneal cavity |

Para-aortic lymph node metastases are considered regional lymph nodes (Stage IIIC). As there is only one para-aortic lymph node intervening before the thoracic duct on the right side of the body, the ovarian cancer can rapidly spread to distant sites such as the lung.

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c). This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body.

The AJCC/TNM staging system also contains a Tx and a Nx sub-category which indicates that the extent of the tumor cannot be described because of insufficient data, respectively the involvement of the lymph nodes cannot be described because of the same reason. The ovarian cancer stages are made up by combining the TNM categories in the following manner:

Stage I: T1+N0+M0; IA: T1a+N0+M0; IB: T1b+N0+M0; IC: T1c+N0+M0;
Stage II: T2+N0+M0; IIa: T2a+N0+M0; IIB: T2b+N0+M0; IIC: T2c+N0+M0;
Stage III: T3+N0+M0; IIIA: T3a+N0+M0; IIIB: T3b+N0+M0; IIIC: T3c+N0+M0 or Any T+N1+M0;
Stage IV: Any T+ Any N+M1

In addition to being staged, like all cancers ovarian cancer is also graded. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

Cancer staging can be divided into a clinical stage and a pathologic stage. In the TNM (Tumor, Node, Metastasis) system, clinical stage and pathologic stage are denoted by a small "c" or "p" before the stage (e.g., cT3N1M0 or pT2N0). Clinical stage is based on all of the available information obtained before a surgery to remove the tumor. Thus, it may include information about the tumor obtained by physical examination, radiologic examination, and endoscopy. Pathologic stage adds additional information gained by examination of the tumor microscopically by a pathologist.

Because they use different criteria, clinical stage and pathologic stage often differ. Pathologic staging is usually considered the "better" or "truer" stage because it allows direct examination of the tumor and its spread, contrasted with clinical staging which is limited by the fact that the information is obtained by making indirect observations of a tumor which is still in the body. However, clinical staging and pathologic staging still has to be complemented by each other. Not every tumor is treated surgically, therefore pathologic staging is not always available. Also, sometimes surgery is preceded by other treatments such as chemotherapy and radiation therapy which shrink the tumor, so the pathologic stage may underestimate the true stage.

This staging system is used for most forms of cancer, except brain tumors and hematological malignancies. For solid tumors, TNM is by far the most commonly used system, but it has been adapted for some conditions.

However, there is a need for improved tools for the early detection; staging, grading and prognosis of cancer, like solid organ cancers, squamous cell carcinoma of the skin and metastatic cancer, as well as ovarian cancer. In particular there is a need for predicting response to a cancer treatment.

SUMMARY OF THE INVENTION

Subject of the invention is a method for diagnosis of a cancer, comprising the steps of
(i) determining the level of antibodies against vascular endothelial growth factor receptor (VEGFR) in a sample from a subject to be diagnosed,
(ii) comparing the determined level in the sample to a control level of antibodies against VEGFR (VEGFR antibody control level) derived from subjects without cancer;
wherein a decreased level in the sample from the subject to be diagnosed as compared to the control level is indicative for cancer in the subject.

The invention further pertains to a method for diagnosis of a cancer, wherein the level of antibodies against vascular endothelial growth factor receptor (VEGFR) is determined in a sample from a subject to be diagnosed and wherein a level of anti-VEGFR antibodies below 43 units/ml is indicative for cancer, preferably below 40, more preferably below 37, further preferred below 35 units/ml.

The present invention is further directed to an immunoassay method for detecting an anti-VEGF antibody in a sample from a subject, comprising the steps of
(a) contacting the sample suspected of comprising an anti-VEGFR antibody with vascular endothelial growth factor receptor (VEGFR) or an antigenic peptide fragment thereof under conditions allowing for the formation of a complex between the anti-VEGFR antibody with VEGFR or the peptide fragment thereof,
(b) detecting the complex.

In the context of the present invention VEGFR or an antigenic peptide fragment thereof can thus be used for the diagnosis of cancer.

The present invention further relates to research and/or diagnostic kit for the diagnosis of cancer or for the prediction of response or non-response in a patient, wherein the kit comprises vascular endothelial growth factor receptor (VEGFR) or an antigenic (immunogenic) peptide fragment thereof.

The inventors also found that the level of antibodies against vascular endothelial growth factor receptor (VEGFR) correlates with the risk of relapse or mortality in subjects treated with an angiogenesis inhibitor. Decreased levels of anti-VEGFR antibodies in samples correlated with a higher risk of relapse and/or mortality in patients treated with said angiogenesis inhibitor. Hence, levels of anti-VEGFR antibodies in samples of patients to be treated with an angiogenesis inhibitor are an indicator for response or non-response of a patient, i.e. whether improvement of the disease is achieved in a patient (responder) or not (non-responder). If a patient responds to a treatment the disease is ameliorated. It might be the case that a patient responds to a treatment at first but suffers from relapse of the disease at a later stage. Also this is a form of non-response. However, it is difficult to predict whether a patient will respond or not to a treatment as it may be determined only at later stages with the known methods, e.g. when relapse, progression or death occurs. This problem is solved by the present invention as it provides a predictive method to predict whether a subject will respond or not to a certain treatment, e.g. a treatment with an angiogenesis inhibitor.

Therefore, the invention also relates to a method for determining whether a subject being treated or to be treated for cancer with a drug will respond to said treatment comprising the steps of
(i) determining the level of antibodies against vascular endothelial growth factor receptor (VEGFR) in a sample from said subject being treated or to be treated,
(ii) comparing the determined level in the sample to either one or both of a first and second VEGFR antibody control level, wherein
  a) the first VEGFR antibody control level is derived from subjects responding to said treatment, and
  b) the second VEGFR antibody control level is derived from a subject not responding to said treatment,
wherein a decreased level in the sample from the subject being treated or to be treated as compared to the first VEGFR antibody control level and/or an equal level as compared to the second VEGFR antibody control level is indicative for a non-response of said subject to said treatment, and wherein an increased level in the sample from the subject being treated or to be treated as compared to the second VEGFR antibody control level and/or an equal level as compared to the first VEGFR antibody control level is indicative for a response of said subject to said treatment. In a preferred embodiment of the invention the subject is to be treated, i.e. the method to determine response of a subject is performed before the onset of treatment. In a preferred embodiment the treatment comprises the administration of a drug, preferably a drug selected from the group of a chemotherapeutic drug and an angiogenesis inhibitor. Preferred chemotherapeutic drugs are platinum analogues. Preferred angiogenesis inhibitors are outlined herein below.

The present invention also relates to a method of treating cancer with an angiogenesis inhibitor in a subject, comprising determining the level of antibodies against vascular endothelial growth factor receptor (VEGFR) in a sample from the subject, wherein when the level of anti-VEGFR antibodies in a sample from the subject is above 6 units/ml, said angiogenesis inhibitor is administered to the subject, preferably above 9 units/ml, more preferably above 12 units/ml, also preferred above 15 units/ml. However, the threshold may also be determined as outlined above, hence, the method of treating cancer in a subject may also comprise the method for determining whether a subject being treated or to be treated for cancer with a drug will respond to said treatment, wherein the drug is administered if the determined levels of VEGFR antibodies in said subject is indicative for response to the drug.

As outlined herein, results of non-response of a patient to a treatment may be relapse or progression of cancer, death (mortality) of the patient. Hence, in a preferred embodiment of the method to determine/predict the response of a subject to a treatment the present invention also relates to a method for the prediction of risk stratification for relapse of cancer and/or mortality in a patient being treated or to be treated for cancer with a drug, the method comprising the steps of (i) determining the level of antibodies against vascular endothelial growth factor receptor (VEGFR) in a sample from said subject being treated or to be treated for cancer with said drug (ii) comparing the determined level in the sample to either one or both of a first and a second VEGFR antibody control level, a) wherein the first VEGFR antibody control level is derived from subjects not showing relapse or progression of cancer or mortality after treatment with said drug, and b) wherein the second VEGFR antibody control level is derived from subjects showing relapse or progression of cancer or mortality after treatment with said drug, wherein a decreased level in the sample from the subject being treated or to be treated as compared to the first VEGFR antibody control level and/or an equal level as compared to the second VEGFR antibody control level is indicative for relapse or progression of cancer or mortality in the subject; and wherein an increased level in the sample from the subject being treated or to be treated as compared to the second VEGFR antibody control level and/or an equal level as compared to the first VEGFR antibody control level is indicative for no response to said treatment, e.g. for no relapse and no progression of cancer and no mortality in the subject. Preferably the level in said patient is determined before the onset of treatment. The preferred subject is therefore in this context a subject to be treated with said drug. In a preferred embodiment of the present invention first VEGFR antibody control level is derived from subjects that did not show relapse or progression of cancer or mortality within 20 months after onset of treatment with said drug and the second VEGFR antibody control level is derived from subjects that did show relapse or progression of cancer or mortality within 20 months after onset of treatment with said drug.

The present invention also relates to a method prediction of risk stratification for relapse of cancer and/or mortality in a patient being treated or to be treated with a drug, comprising determining the level of antibodies against vascular endothelial growth factor receptor (VEGFR) in a sample from the subject, wherein when the level of anti-VEGFR antibodies in a sample from the subject is below 46 units/ml, is indicative for relapse or progression of cancer or mortality in the subject.

As will be readily understood by the skilled person, this method may be performed as a method for monitoring cancer treatment efficiency. In this embodiment the levels of anti-VEGFR antibodies in said subject is determined during treatment, i.e. in a subject being treated with said drug.

DETAILED DESCRIPTION OF THE INVENTION

Figure 1:
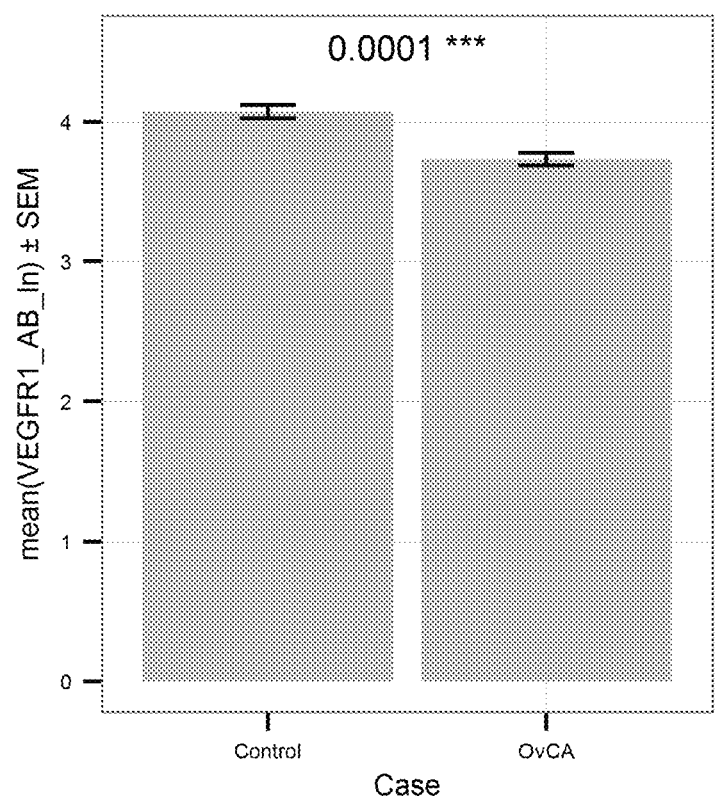
FIG. 1: Comparison of the mean level of anti-VEGFR antibodies (ln of units/ml) in serum samples of ovarian cancer patients (OvCA; ln of mean=3.733; n=201) to the mean level of anti-VEGFR antibodies in serum samples of a healthy control group (Control, ln of mean=4.073 units/ml; n=130). The p-value is indicated on top. Bars indicate standard error of mean.

The present invention is based on the surprising finding of the inventors that in samples of patients with cancer (e.g. ovarian cancer, solid organ cancer, squamous cell carcinoma or metastatic cancer) decreased levels of anti-VEGFR antibodies can be found as compared to subjects without cancer. In other words the inventors have found that patients with cancer have little or no detectable antibodies against vascular endothelial growth factor receptor (VEGFR) in the blood (e.g. determined in serum), whereas in control groups anti-VEGFR auto-antibodies can be detected at higher levels.

The present invention is based on the finding of that levels of autoimmune-antibodies in subjects have diagnostic and predictive properties. The antibodies to be detected in connection with the present invention are therefore autoantibody, i.e. those produced by immune system of the subject to be diagnosed or being or to be treated.

The invention relates to a method for the diagnosis of a cancer, comprising the steps of
(i) determining the level of antibodies against VEGFR in a sample from a subject to be diagnosed,
(ii) comparing the determined level in the sample to a control level of antibodies against VEGFR in samples derived from subjects without cancer;
wherein a decreased level in the sample from the subject to be diagnosed as compared to the control level is indicative for cancer in the subject.

Preferably, the cancer according to the present invention is a VEGF or VEGFR associated cancer, preferably selected from the group consisting of ovarian cancer, a solid organ cancer, squamous cell carcinoma of the skin, metastatic cancer, breast cancer, lung cancer, colon cancer, renal (kidney) cancer, pancreatic cancer, liver cancer, prostate cancer, gastric cancer, a glioblastoma and colorectal cancer. Particularly preferred the cancer is selected from the group consisting of ovarian cancer, a solid organ cancer, squamous cell carcinoma of the skin, and metastatic cancer, more preferred ovarian cancer. It will be understood by those of ordinary skills in the art, that if a preferred cancer is chose to be diagnosed, the control level should be derived from subjects without that specific cancer, i.e. if ovarian cancer is to be diagnosed, the control level shall be derived from subjects without ovarian cancer. However, as has been shown in the Examples, the levels of VEGFR antibodies are decreased in various types of cancer. Hence, in a particularly preferred embodiment of the method for diagnosis of cancer the control level is derived from subjects without any cancer.

Hence, the invention relates to a method for the diagnosis of a cancer selected from the group consisting of ovarian cancer, a solid organ cancer, squamous cell carcinoma of the skin, and metastatic cancer, comprising the steps of (i) determining the level of antibodies against VEGFR in a sample from a subject to be diagnosed, (ii) comparing the determined level in the sample to a control level of antibodies against VEGFR in samples derived from subjects without cancer; wherein a decreased level in the sample from the subject to be diagnosed as compared to the control level is indicative for cancer in the subject selected from the group consisting of ovarian cancer, a solid organ cancer, squamous cell carcinoma of the skin, and metastatic cancer. Further, the invention relates to a method for the diagnosis of ovarian cancer, comprising the steps of (i) determining the level of antibodies against VEGFR in a sample from a subject to be diagnosed, (ii) comparing the determined level in the sample to a control level of antibodies against VEGFR in samples derived from subjects without cancer; wherein a decreased level in the sample from the subject to be diagnosed as compared to the control level is indicative for ovarian cancer in the subject to be diagnosed.

As can be derived from FIG. 1, the ln of the mean level of VEGFR antibodies in patients suffering from ovarian cancer is 3.733 (=41.8 units/ml) and in healthy subjects 4.073 (=58.73 units/ml). Hence, in one embodiment a level of less than 0.9 fold as compared to the control level from subjects without cancer is indicative for the presence of cancer, preferably a level of less than 0.8 fold, more preferably of less than 0.75 fold. The cancer is preferably a VEGF and VEGF-receptor (VEGFR) associated cancer as defined herein. Particularly preferred is ovarian cancer. The skilled person will acknowledge that in case a certain cancer is to be diagnosed, the control level is preferably derived from subjects not having this particular cancer. As can be derived from the examples provided herein, the ratio may be even lower for different types of cancers, e.g. metastatic cancers (about 0.68 fold compared to the control level from subjects without cancer), solid organ cancer (about 0.55 fold compared to the control level from subjects without cancer), or squamous cell cancer (about 0.53 fold compared to the control level from subjects without cancer). Hence, in one embodiment a level of less than 0.7 fold as compared to the control level from subjects without cancer is indicative for the presence of a cancer, selected from the group consisting of metastatic cancer, solid organ cancer, and squamous cell cancer. In a further embodiment a level of less than 0.6 fold as compared to the control level from subjects without cancer is indicative for the presence of a cancer, selected from the group consisting of solid organ cancer, and squamous cell cancer.

The skilled artisan will understand that the diagnosis of cancer is performed in order to evaluate whether the patient is to be treated for cancer. Hence, in a preferred embodiment of the method for diagnosis, the subject to be diagnosed is treated for cancer if the VEGFR antibody levels in said subject to be treated are indicative for the presence of cancer.

The invention further pertains to a method for diagnosis of a ovarian cancer, wherein the level of antibodies against vascular endothelial growth factor receptor (VEGFR) is determined in a sample from a subject to be diagnosed and wherein a level of anti-VEGFR antibodies below 43 units/ml is indicative for ovarian cancer, preferably below 40, more preferably below 37 units/ml, further preferred below 35 units/ml. The levels as mentioned in this paragraph preferably relate to levels in serum samples. Hence, in one embodiment the invention further pertains to a method for diagnosis of a ovarian cancer, wherein the level of antibodies against vascular endothelial growth factor receptor (VEGFR) is determined in a serum sample from a subject to be diagnosed and wherein a level of anti-VEGFR antibodies below 43 units/ml is indicative for ovarian cancer, preferably below 40, more preferably below 37 units/ml, further preferred below 35 units/ml. In a further embodiment the invention further pertains to a method for diagnosis of a cancer, wherein the level of antibodies against vascular endothelial growth factor receptor (VEGFR) is determined in a plasma sample from a subject to be diagnosed and wherein a level of anti-VEGFR antibodies below 7.5 units/ml is indicative for a cancer, preferably for a cancer selected from the group consisting of metastatic cancer, solid organ cancer, and squamous cell cancer, preferably a level of anti-VEGFR antibodies below 6 units/ml is indicative for a cancer, preferably for a cancer selected from the group consisting of metastatic cancer, solid organ cancer, and squamous cell cancer. Further preferred a level of anti-VEGFR antibodies below 5 units/ml is indicative for a cancer, preferably for a cancer selected from the group consisting of metastatic cancer, solid organ cancer, and squamous cell cancer, more preferably a level of anti-VEGFR antibodies below 5 units/ml is indicative for a cancer selected from the group consisting of solid organ cancer, and squamous cell cancer.

The inventors also found that differential diagnosis as to the grade (differentiation) of cancer, particularly for solid organ cancers like ovarian cancer, is possible when using the method according to the present invention. Hence, the present invention also relates to a method for differential diagnosis of a cancer, preferably a solid organ cancer, comprising the steps of
(i) determining the level of antibodies against vascular endothelial growth factor receptor (VEGFR) in a sample from a subject to be diagnosed,
(ii) comparing the determined level in the sample to either one or both of a first and second VEGFR antibody control level,
  a) wherein the first VEGFR antibody control level is derived from subjects suffering from a cancer classified as Grade II or Grade III cancer, preferably Grade II or Grade III solid organ cancer, and
  b) wherein the second VEGFR antibody control level is derived from a subject suffering from an cancer classified as Grade I cancer, preferably Grade I solid organ cancer,
wherein a increased level in the sample from the subject to be diagnosed as compared to the first VEGFR antibody control level and/or an equal level as compared to the second VEGFR antibody control level is indicative for Grade I cancer, preferably Grade I solid organ cancer, in said subject to be diagnosed, and wherein an decreased level in the sample from the subject to be diagnosed as compared to the second VEGFR antibody control level and/or an equal level as compared to the first VEGFR antibody control level is indicative for Grade II or Grade III cancer, preferably Grade II or III solid organ cancer, in said subject to be diagnosed. This method in one embodiment is a method for differentiating between Grade I and Grade II or Grade III cancer, preferably Grade I solid organ cancer. It is apparent that thereby the present invention provides a method for differentiating between histological grades of tumors without the necessity of surgical intervention. Hence, in one embodiment of the method for differential diagnosis, the method is preformed without surgical treatment and histological analysis. However, the present invention may also be used to assist histological analysis and may hence be used in parallel. Nevertheless, surgical biopsy and histological analysis are not part of the invention. The levels indicative may be determined using the method above, i.e. using control levels, which may be determined by the skilled person when considering the disclosure of the present invention.

The method for differential diagnosis of cancer may also be conducted using ratios. Hence, in one embodiment of the methods for differential diagnosis of a cancer a level of antibodies against VEGFR in the sample from the subject to be diagnosed of less than 0.9 fold as compared to the second VEGFR antibody control level is indicative for Grade II or Grade III cancer in said subject to be diagnosed, preferably a level of antibodies against VEGFR in the sample from the subject to be diagnosed of less than 0.85 fold as compared to the second VEGFR antibody control level is indicative for Grade II or Grade III cancer in said subject to be diagnosed, more preferably a level of antibodies against VEGFR in the sample from the subject to be diagnosed of less than 0.8 fold as compared to the second VEGFR antibody control level is indicative for Grade II or Grade III cancer in said subject to be diagnosed. Likewise, ratios may be determined with respect to the first antibody control level. In such embodiment which may be used in addition or as an alternative to the ratio of the second control level, a level of antibodies against VEGFR in the sample from the subject to be diagnosed of more than 1.1 fold as compared to the first VEGFR antibody control level is indicative for Grade I cancer in said subject to be diagnosed, preferably a level of antibodies against VEGFR in the sample from the subject to be diagnosed of more than 1.2 fold as compared to the first VEGFR antibody control level is indicative for Grade I cancer in said subject to be diagnosed, more preferably a level of antibodies against VEGFR in the sample from the subject to be diagnosed of more than 1.3 fold as compared to the first VEGFR antibody control level is indicative for Grade I cancer in said subject to be diagnosed.

The data presented in particular outline the differential diagnosis for a solid organ cancer, e.g. ovarian cancer. Hence, the present invention also relates to a method for differential diagnosis of ovarian cancer comprising the steps of
(i) determining the level of antibodies against vascular endothelial growth factor receptor (VEGFR) in a sample from a subject to be diagnosed,
(ii) comparing the determined level in the sample to either one or both of a first and second VEGFR antibody control level,
   a) wherein the first VEGFR antibody control level is derived from subjects suffering from an ovarian cancer classified as Grade II or Grade III ovarian cancer, and
   b) wherein the second VEGFR antibody control level is derived from a subject suffering from an ovarian cancer classified as Grade I ovarian cancer,
wherein a increased level in the sample from the subject to be diagnosed as compared to the first VEGFR antibody control level and/or an equal level as compared to the second VEGFR antibody control level is indicative for Grade I ovarian cancer in said subject to be diagnosed, and wherein an decreased level in the sample from the subject to be diagnosed as compared to the second VEGFR antibody control level and/or an equal level as compared to the first VEGFR antibody control level is indicative for Grade II or Grade III ovarian cancer in said subject to be diagnosed. This method in one embodiment is a method for differentiating between Grade I and Grade II or Grade III ovarian cancer. It is apparent that thereby the present invention provides a method for differentiating between histological grades of tumors without the necessity of surgical intervention. Hence, in one embodiment of the method for differential diagnosis, the method is preformed without surgical treatment and histological analysis. However, the present invention may also be used to assist histological analysis and may hence be used in parallel. Nevertheless, surgical biopsy and histological analysis are not part of the invention. The levels indicative may be determined using the method above, i.e. using control levels, which may be determined by the skilled person when considering the disclosure of the present invention. However, in a preferred embodiment a level of 30 units/ml or less is indicative for Grade II or Grade III ovarian cancer and levels of 30 units/ml or more are indicative for Grade I ovarian cancer. The method for differential diagnosis of ovarian cancer may also be conducted using ratios. Hence, in one embodiment of the methods for differential diagnosis of a cancer a level of antibodies against VEGFR in the sample from the subject to be diagnosed of less than 0.9 fold as compared to the second VEGFR antibody control level is indicative for Grade II or Grade III ovarian cancer in said subject to be diagnosed, preferably a level of antibodies against VEGFR in the sample from the subject to be diagnosed of less than 0.85 fold as compared to the second VEGFR antibody control level is indicative for Grade II or Grade III ovarian cancer in said subject to be diagnosed, more preferably a level of antibodies against VEGFR in the sample from the subject to be diagnosed of less than 0.8 fold as compared to the second VEGFR antibody control level is indicative for Grade II or Grade III ovarian cancer in said subject to be diagnosed. Likewise, ratios may be determined with respect to the first antibody control level. In such embodiment which may be used in addition or as an alternative to the ratio of the second control level, a level of antibodies against VEGFR in the sample from the subject to be diagnosed of more than 1.1 fold as compared to the first VEGFR antibody control level is indicative for Grade I ovarian cancer in said subject to be diagnosed, preferably a level of antibodies against VEGFR in the sample from the subject to be diagnosed of more than 1.2 fold as compared to the first VEGFR antibody control level is indicative for Grade I ovarian cancer in said subject to be diagnosed, more preferably a level of antibodies against VEGFR in the sample from the subject to be diagnosed of more than 1.3 fold as compared to the first VEGFR antibody control level is indicative for Grade I ovarian cancer in said subject to be diagnosed.

Furthermore, ratios of determined levels compared to the controls may be used in connection with the method for determining response or non-response to a treatment with a drug, preferably an angiogenesis inhibitor as defined herein, preferably bevacizumab. In this embodiment the determined level of antibodies in the method for determining whether a subject being treated or to be treated for cancer with a drug will respond to said treatment are compared to the control levels in terms of ratios. The method as outlined herein comprises the steps of
(i) determining the level of antibodies against vascular endothelial growth factor receptor (VEGFR) in a sample from said subject being treated or to be treated,
(ii) comparing the determined level in the sample to either one or both of a first and second VEGFR antibody control level, wherein
   a) the first VEGFR antibody control level is derived from subjects responding to said treatment, and
   b) the second VEGFR antibody control level is derived from a subject not responding to said treatment,
wherein a decreased level in the sample from the subject being treated or to be treated as compared to the first VEGFR antibody control level and/or an equal level as compared to the second VEGFR antibody control level is indicative for a non-response of said subject to said treatment, and wherein an increased level in the sample from the subject being treated or to be treated as compared to the second VEGFR antibody control level and/or an equal level as compared to the first VEGFR antibody control level is indicative for a response of said subject to said treatment. In a preferred embodiment of the invention the subject is to be treated, i.e. the method to determine response of a subject is performed before the onset of treatment. In a preferred embodiment the treatment comprises the administration of a drug, preferably a drug selected from the group of a chemotherapeutic drug and an angiogenesis inhibitor. Preferred chemotherapeutic drugs are platinum analogues. Preferred angiogenesis inhibitors are outlined herein below. In such embodiment comparing the levels in terms of ratios, a level of antibodies against VEGFR in the sample from the subject to be treated of less than 0.9 fold as compared to the first VEGFR antibody control level is indicative for a non-response of said subject to said treatment, preferably a level of antibodies against VEGFR in the sample from the subject to be treated of less than 0.5 fold as compared to the first VEGFR antibody control level is indicative for a non-response of said subject to said treatment, further preferred a level of antibodies against VEGFR in the sample from the subject to be treated of less than 0.3 fold as compared to the first anti-VEGFR control level is indicative for a non-response of said subject to said treatment. Likewise, ratios may be determined for the response. In such embodiment a level of antibodies against VEGFR in the sample from the subject to be treated of more than 1.5 fold as compared to the second VEGFR antibody control level is indicative for a response of said subject to said treatment, preferably a level of antibodies against VEGFR in the sample from the subject to be treated of more than 3.0 fold as compared to the second VEGFR antibody control level is indicative for a response of said subject to said treatment, further preferred a level of antibodies against VEGFR in the sample from the subject to be treated of more than 4.0 fold as compared to the second anti-VEGFR control level is indicative for a response of said subject to said treatment. The treatment and response preferably relate to an inhibitor of angiogenesis as defined herein, preferably bevacizumab. Furthermore, ratios may be determined when comparing the determined levels to the control levels. Hence, the invention also relates to a method of treating cancer in a subject with a drug, preferably with an angiogenesis inhibitor, e.g. bevacizumab, comprising determining the level of antibodies against vascular endothelial growth factor receptor (VEGFR) in a sample from the subject to be treated and comparing the determined level in the sample to either one or both of a first and second VEGFR antibody control level, wherein
  a) the first VEGFR antibody control level is derived from subjects responding to said treatment, and
  b) the second VEGFR antibody control level is derived from a subject not responding to said treatment,
wherein the drug is administered to the subject to be treated when a level of antibodies against VEGFR in the sample from the subject to be treated of less than 0.9 fold, preferably less than 0.5 fold, more preferably less than 0.3 fold, as compared to the first VEGFR antibody control level is determined, and/or when a level of antibodies against VEGFR in the sample from the subject to be treated of more than 1.5 fold, preferably more than 3.0 fold, more preferably more than 4.0 fold, as compared to the second VEGFR antibody control level is determined. In a preferred embodiment the cancer to be treated is selected from the group of cancers as defined herein. In a particular embodiment the cancer is ovarian cancer. In such embodiment the invention also relates to a method of treating ovarian cancer in a subject with a drug, preferably with an angiogenesis inhibitor, e.g. bevacizumab, comprising determining the level of antibodies against vascular endothelial growth factor receptor (VEGFR) in a sample from the subject to be treated and comparing the determined level in the sample to either one or both of a first and second VEGFR antibody control level, wherein
  a) the first VEGFR antibody control level is derived from subjects responding to said treatment, and
  b) the second VEGFR antibody control level is derived from a subject not responding to said treatment,
wherein the drug is administered to the subject to be treated when a level of antibodies against VEGFR in the sample from the subject to be treated of less than 0.9 fold, preferably less than 0.5 fold, more preferably less than 0.3 fold, as compared to the first VEGFR antibody control level is determined, and/or when a level of antibodies against VEGFR in the sample from the subject to be treated of more than 1.5 fold, preferably more than 3.0 fold, more preferably more than 4.0 fold, as compared to the second VEGFR antibody control level is determined.

Auto-antibodies directed against VEGFR are not known until today. The inventors of the present application for the first time demonstrate the presence of such antibodies as well as the diagnostic and predictive value. It was found that a decrease in the level of antibodies directed against VEGFR in samples of a subject to be diagnosed as compared samples from subjects with proven absence of cancer is indicative for the presence of cancer as well as for the prediction of response or non-response to a treatment of the cancer with a drug. Hence, "cancer" in connection with the present invention is to be understood as any diseases involving unregulated cell growth. Cancer in this regard is a disease where cells divide and grow uncontrollably resulting in the formation of malignant tumors.

However, in a preferred embodiment of the present invention "cancer" refers to an epithelial cancer, preferably VEGF and VEGF-receptor (VEGFR) associated cancer. In a particularly preferred embodiment the term "cancer" refers to a disease selected from the group consisting of ovarian cancer, solid organ cancer, squamous cell carcinoma, and metastatic cancer. VEGF and VEGFR associated cancers are known by the skilled person. VEGF has been implicated with poor prognosis in cancer. Numerous studies show a decreased overall survival and disease-free survival in those tumors overexpressing VEGF. The overexpression of VEGF may be an early step in the process of metastasis, a step that is involved in the "angiogenic" switch. Although VEGF has been correlated with poor survival, its exact mechanism of action in the progression of tumors remains unclear. Once released, VEGF elicits several responses. It causes a cell to survive, move, or further differentiate. Hence, VEGF is a target for the treatment of cancer. The first anti-VEGF drug, a monoclonal antibody named bevacizumab, was approved in 2004. Approximately 10-15% of patients benefit from bevacizumab therapy; however, biomarkers for bevacizumab efficacy are not yet known. Anti-VEGF therapies are important in the treatment of certain cancers. They involve monoclonal antibodies such as bevacizumab (Avastin), antibody derivatives such as ranibizumab (Lucentis), or orally-available small molecules that inhibit the tyrosine kinases stimulated by VEGF: lapatinib (Tykerb), sunitinib (Sutent), sorafenib (Nexavar), axitinib, and pazopanib. Some of these therapies target VEGF receptors rather than the VEGFs.

Squamous-cell carcinoma or squamous cell cancer (SCC or SqCC) is a cancer of a kind of epithelial cell, the squamous cell. These cells are the main part of the epidermis of the skin, and this cancer is one of the major forms of skin cancer. However, squamous cells also occur in the lining of the digestive tract, lungs, and other areas of the body, and SCC occurs as a form of cancer in diverse tissues, including the lips, mouth, esophagus, urinary bladder, prostate, lung, vagina, and cervix, among others. SCC is a histologically distinct form of cancer. It arises from the uncontrolled multiplication of cells of epithelium, or cells showing particular cytological or tissue architectural characteristics of squamous cell differentiation, such as the presence of keratin, tonofilament bundles, or desmosomes, structures involved in cell-to-cell adhesion. SCC is still sometimes referred to as "epidermoid carcinoma" and "squamous cell epithelioma", though the use of these terms has decreased. SCC typically initially occurs in the sixth decade of life (the 50s), but is most common in the eighth decade (the 70s). It is twice as prevalent in men as in women. People with darker skin are less at risk to develop SCC. Populations with fair skin, light hair, and blue/green/grey eyes are at highest risk of developing the disease. Frequent exposure to direct, strong sunlight without adequate topical protection also increases risk. SCC as referred to herein refers to a squamous cell carcinoma in general, preferably selected from the group of squamous cell carcinoma of the skin, the digestive tract, the lung, the lips, the mouth, the esophagus, the urinary bladder, the prostate, the lung, the vagina, and the cervix, more preferably it refers to squamous cell carcinoma of the skin.

VEGF receptors are receptors for vascular endothelial growth factor (VEGF) (Holmes K, Roberts O L, Thomas A M, Cross M J. (October 2007). "Vascular endothelial growth factor receptor-2: structure, function, intracellular signaling and therapeutic inhibition." Cell Signal. 19 (10): 2003-2012; Stuttfeld E, Ballmer-Hofer K (September 2009) "Structure and function of VEGF receptors". IUBMB Life 61 (9): 915-22). There are three main subtypes of VEGFR, numbered VEGFR-1, VEGFR-2 and VEGFR-3. Also, they may be membrane-bound (mbVEGFR) or soluble (sVEGFR), depending on alternative splicing (Fujita, N.; Imai, J.; Suzuki, T.; Yamada, M.; Ninomiya, K.; Miyamoto, K.; Iwasaki, R.; Morioka, H.; Matsumoto, M.; Chiba, K.; Watanabe, S.; Suda, T.; Toyama, Y.; Miyamoto, T. (2008). "Vascular endothelial growth factor-A is a survival factor for nucleus pulposus cells in the intervertebral disc". Biochemical and Biophysical Research Communications 372 (2): 367-372). All members of the VEGF family stimulate cellular responses by binding to tyrosine kinase receptors (the VEGFRs) on the cell surface, causing them to dimerize and become activated through transphosphorylation. The VEGF receptors have an extracellular portion consisting of 7 immunoglobulin-like domains, a single transmembrane spanning region and an intracellular portion containing a split tyrosine-kinase domain.

VEGF-A binds to VEGFR-1 (also known as Flt-1) and VEGFR-2 (also known as KDR/Flk-1). VEGFR-2 mediate almost all of the known cellular responses to VEGF (Holmes K, Roberts O L, Thomas A M, Cross M J. (October 2007). "Vascular endothelial growth factor receptor-2: structure, function, intracellular signaling and therapeutic inhibition." Cell Signal. 19 (10): 2003-2012). The function of VEGFR-1 is, inter alia, to modulate VEGFR-2 signaling. Another function of VEGFR-1 is to act as a dummy/decoy receptor, sequestering VEGF from VEGFR-2 binding (this appears to be particularly important during vasculogenesis in the embryo). In fact, an alternatively spliced form of VEGFR-1 (sFlt1) is not a membrane bound protein but is secreted and functions primarily as a decoy (Zygmunt T, Gay C M, Blondelle J, Singh M K, Flaherty K M, Means P C, Herwig L, Krudewig A, Belting H G, Affolter M, Epstein J A, Torres-Vázquez J. (August 2011). "Semaphorin-PlexinD1 Signaling Limits Angiogenic Potential via the VEGF Decoy Receptor sFlt1". Dev Cell. 21 (2): 301-314). A third receptor has been discovered (VEGFR-3), however, VEGF-A is not a ligand for this receptor. VEGFR-3 (also known as Flt-4) mediates lymphangiogenesis in response to VEGF-C and VEGF-D.

In a preferred embodiment of the present invention the cancer is an selected from the group consisting of ovarian cancer, colorectal cancer, colon cancer, lung cancer, ovarian cancer, breast cancer, glioblastoma, and kidney cancer, pancreatic cancer, liver cancer, prostate cancer, and gastric cancer. In a particularly preferred embodiment the cancer according to the present invention, including all embodiments, is an ovarian cancer. Ovarian cancer often derives from the epithelium of the ovary, but may also be derived from fallopian tube. However, it was found that in both cases the method of the present invention is predictive for the presence of cancer or the response to a certain treatment. Hence, in one embodiment of the present invention cancer is an ovarian cancer, the ovarian cancer being epithelial ovarian cancer or cancer derived from the fallopian tube.

The skilled person knows that depending on the subject, different cancers may be diagnosed. He is aware that he also may have to consider further parameters to diagnose the subject, e.g. when diagnosing ovarian cancer, the subject has to be female. In the context of the present invention the subject to be diagnosed is a mammal, preferably a human. In a further preferred embodiment the subject is a female mammal, preferably a female human subject suspected of having ovarian cancer or a female mammal, preferably a female human subject to be screened for the presence of ovarian cancer, preferably a female human subject to be treated or being treated for ovarian cancer with a drug.

The invention particularly relates to a method for diagnosis of ovarian cancer, wherein the level of antibodies against VEGFR is determined in a sample from a subject to be diagnosed and wherein a level of anti-VEGFR antibodies below 43 units/ml is indicative for ovarian cancer, preferably below 40, more preferably below 37, further preferred below 35 units/ml. In the context of the present invention the term "VEGFR" and "VEGF-receptor" or simply "the receptor" relates to the "vascular endothelial growth factor receptor"

Vascular endothelial growth factor receptors (VEGFR) are receptors for VEGF which is a signal protein stimulating vasculogenesis and angiogenesis. VEGF's normal function is to create new blood vessels during embryonic development, new blood vessels after injury, muscle following exercise, and new vessels (collateral circulation) to bypass blocked vessels. Overexpression or missregulation of VEGF or VEGFR contributes to diseases. Cancers in order to allow growth beyond a certain size need supply blood. Many tumors express VEGF in order to grow and metastasize. Overexpression of VEGF can cause vascular disease in the retina of the eye and other parts of the body. Drugs such as bevacizumab and other angiogenesis inhibitors can inhibit VEGF and thereby VEGFR and control or slow those diseases.

VEGF is a sub-family of growth factors, to be specific, the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature). VEGF includes VEGF-A, VEGF-B, VEGF-C, VEGF-D and Placenta growth factor (PIGF). Before the discovery of VEGF-B to D and PIGF, VEGF-A was the only known VEGF. VEGF-A was called just VEGF at these days. These VEGF subtypes have similar activities. However, VEGF-A plays crutial roles in angiogenesis, migration of endothelial cells, mitosis of endothelial cells, methane monooxygenase activity, $\alpha v \beta 3$ activity, creation of blood vessel lumen, creates fenestrations, chemotactic for macrophages and granulocytes, vasodilation (indirectly by NO release). VEGF-B is particularly involved in embryonic angiogenesis (myocardial tissue, specifically) (Claesson-Welsh, L. (2008). "VEGF-B Taken to Our Hearts: Specific Effect of VEGF-B in Myocardial Ischemia". Arteriosclerosis, Thrombosis, and Vascular Biology 28 (9): 1575-1576). VEGF-C regulats lymphangiogenesis, while VEGF-D is needed for the development of lymphatic vasculature surrounding lung bronchioles. Recently, VEGF-C has been shown to be an important inducer of neurogenesis in the murine subventricular zone, without exerting angiogenic effects (Shin, Y. J., J. S. Choi, et al. (2010). "Induction of vascular endothelial growth factor receptor-3 mRNA in glial cells following focal cerebral ischemia in rats." J Neuroimmunol 229(1-2):

81-90). PlGF is important for vasculogenesis, and also needed for angiogenesis during ischemia, inflammation, wound healing, and cancer.

The term "VEGFR" in context of the present invention relates to all subtypes of VEGFR. In a preferred embodiment the VEGFR according to the present invention is VEGFR-1, preferably selected from the group of sVEGFR-1, mbVEGFR-1. Sequences of the recited VEGFR are known to the skilled person. In a preferred embodiment the VEGFR of the present invention have the a sequence selected from the group consisting of SEQ ID NO:1 (sVEGFR-1), and SEQ ID NO:2 (mbVEGFR-1), preferably the sequence of SEQ ID NO:1. Hence, the anti-VEGFR antibodies in the samples as mentioned herein preferably bind to one or any of the mentioned VEGFR, preferably to sVEGFR-1 and/or mbVEGFR-1.

In the context of the immunoassays of the present invention the "VEGFR" may be present in its natural cellular environment and can be used together with the material associated with VEGFR in its natural state as well as in isolated form with respect to its primary, secondary and tertiary structures. The VEGFR is well known to those skilled in the art. The receptor is preferably used in isolated form, i.e. essentially free of other proteins, lipids, carbohydrates or other substances naturally associated with VEGFR. "Essentially free of" means that the receptor is at least 75%, preferably at least 85%, more preferably at least 95% and especially preferably at least 99% free of other proteins, lipids, carbohydrates or other substances naturally associated with the receptor.

In connection with the present invention, the naturally occurring receptor as well as all modifications, mutants or derivatives of the VEGFR can be used. Similarly, a VEGFR produced by means of recombinant techniques, which includes amino acid modifications, such as inversions, deletions, insertions, additions etc. can be used according to the invention provided that this part of the essential function of the VEGFR is present, namely the capability of binding antibodies. The VEGFR being used may also comprise exceptional amino acids and/or modifications of such as alkylation, oxidation, thiol-modification, denaturation, oligomerization and the like. The VEGFR can also be synthesized by chemical means. According to the invention the VEGFR particularly can be a protein and/or peptide or a fusion protein, which in addition to other proteins, peptides or fragments thereof, includes the VEGFR as a whole or in part. Using conventional methods, peptides or polypeptides of the VEGFR which have functionally analogs, analogous properties can be determined by those skilled in the art. For example such polypeptides or peptides have 50-60%, 70% or 80%, preferably 90%, more preferably 95%, and most preferably 98% sequence homology to peptides identified as VEGFR, and said homology can be determined, e.g. by means of Smith-Waterman homology search algorithm, using the MPFRCH program (Oxford Molecular), for example.

The term "peptide" or "polypeptide" of an VEGFR used in the present invention, comprises also molecules differing from the original sequence by deletion(s), insertion(s), substitution(s) and/or other modifications well known in the prior art and/or comprising a fragment of the original amino acid molecule, the VEGFR still exhibiting the properties mentioned above. Such a peptide has preferably at least a length of 100 amino acid residues but may also be shorter, e.g. at least 12, 15, 20 or 25 amino acid residues in length. Also included are allele variants and modifications. Methods of producing the above changes in the amino acid sequence are well known to those skilled in the art and have been described in the standard textbooks of molecular biology, e.g. Sambrook et al., supra. Those skilled in the art will also be able to determine whether a VEGFR, thus, modified still has the properties mentioned above. The amino acid sequence of VEGFR is known. Database entries exist in several well known Databases. When refereeing to the amino acid sequence of VEGFR any amino acid sequence known is meant, particularly those disclosed in common databases, preferably of human origin. The gene which encodes the epidermal growth factor encodes for a larger protein. Preferred sequences of VEGFR are given above, e.g. SEQ ID NO:1 and SEQ ID NO:2. The VEGFR may be glycosylated in vivo. In the present specification all of the above illustrated modifications of the VEGFR will be referred to as "functionally analogous peptides or proteins" in brief The antibodies to be detected or determined according to the present invention are directed against VEGFR. This means that the antibodies specifically bind VEGFR. Specific binding of an antibody normally occurs via binding of a binding site of the antigen. The antibodies of the present invention are those specifically binding to VEGFR or immunogenic fragments thereof. This binding may occur via recognition of sequence or structural epitopes. The skilled person is aware of methods of how to determine specific epitopes, e.g. fragments of the antigen VEGFR, which are recognized and bound by the antibodies to be determined. Fragments of VEGFR binding to the auto antibodies are called immunogenic or antigenic fragments. Methods for determining fragments of an antigen binding the antibody are described in several publications (e.g. Gershoni, J M; Roitburd-Berman, A; Siman-Tov, D D; Tarnovitski Freund, N; Weiss, Y (2007). "Epitope mapping: The first step in developing epitope-based vaccines". BioDrugs 21 (3): 145-56; Westwood, M R; Hay, F C (2001). Epitope Mapping: a practical approach. Oxford, Oxfordshire: Oxford University Press. ISBN 0-19-963652-4; Flanagan et al. (2011), "Mapping Epitopes with H/D-Ex Mass Spec". Genetic Engineering and Biotechnology news; 31(1); Gaseitsiwe, S.; Valentini, D.; Mandavifar, S.; Reilly, M.; Ehrnst, A.; Maeurer, M. (2009) "Peptide Microarray-Based Identification of *Mycobacterium tuberculosis* Epitope Binding to HLA-DRB1*0101, DRB1*1501, and DRB1*0401". Clinical and Vaccine Immunology 17 (1): 168-75; Linnebacher, Michael; Lorenz, Peter; Koy, Cornelia; Jahnke, Annika; Born, Nadine; Steinbeck, Felix; Wollbold, Johannes; Latzkow, Tobias et al. (2012). "Clonality characterization of natural epitope-specific antibodies against the tumor-related antigen topoisomerase IIa by peptide chip and proteome analysis: A pilot study with colorectal carcinoma patient samples" Analytical and Bioanalytical Chemistry 403 (1): 227-38; Cragg, M. S. (2011). "CD20 antibodies: Doing the time warp". Blood 118 (2): 219-20; Banik, Soma S. R.; Doranz, Benjamin J. (2010). "Mapping Complex Antibody Epitopes". Genetic Engineering and Biotechnology News 3 (2): 25-8; and Paes, Cheryl; Ingalls, Jada; Kampani, Karan; Sulli, Chidananda; Kakkar, Esha; Murray, Meredith; Kotelnikov, Valery; Greene, Tiffani A. et al. (2009). "Atomic-Level Mapping of Antibody Epitopes on a GPCR". Journal of the American Chemical Society 131 (20): 6952-4). In context with the present invention anti-VEGFR antibodies are understood as any immunoglobulin specifically recognizing/binding to VEGF, preferably sVEGFR-1 and/or mbVEGFR-1. The antibody in a preferred embodiment binds any of sVEGFR-1 and mbVEGFR-1, preferably to any of a sequence selected from the group consisting of SEQ ID NO:1, and SEQ ID NO:2; preferably to SEQ ID NO:1.

In the context of the present invention the anti-VEGFR antibody may particularly be selected from the group of IgA-antibody, IgG-antibody and IgM-antibody, preferably an IgG antibody, e.g. IgG1, IgG2, IgG3 and IgG4.

Herein, the sample of the subject to be diagnosed in which the level of anti-VEGFR antibodies is to be determined is preferably a bodily fluid such as whole blood or lymph or fractions of blood such as serum or plasma. Preferably in the context of the present invention the sample is plasma or serum. As derivable from the examples, antibody levels for anti-VEGFR antibodies are higher in serum samples than in plasma. However, the skilled artisan will also recognize that this does not interfere with the applicability of the methods according to the present invention. In a preferred embodiment the sample in which the level of anti-VEGFR antibodies is to be detected is the same as the sample from which the control levels are derived. That is, if the levels are detected in a plasma sample of the subject to be diagnosed, the determined levels should be compared to control levels derived from plasma samples of the respective control subject. It is also clear from the results provided herewith, that the nature of the so chosen sample does not change the ratio of the levels in cancer patients when comparing them to the control levels measured in the same type of sample.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, and dialysis. Pre-treatments may also include the addition of chemical or biochemical substances to the solution, such as acids, bases, buffers, salts, solvents, reactive dyes, detergents, emulsifiers, chelators.

The control levels as disclosed herein refer to control levels of VEGFR antibodies. It will be readily understood by the skilled person that the control levels from subjects having the desired disease or response as defined in the methods and to which the determined levels are compared to, are not necessarily determined in parallel but may be represented by previously determined levels. Nevertheless, control levels may be determined in parallel. The skilled person with the disclosure of the present invention and his knowledge is able to determine such levels, as will be outlined herein below. Hence, the control levels of the present invention may be previously defined thresholds. Preferred thresholds are disclosed herein. Furthermore, it will be acknowledged by the skilled person that control levels are, like the levels to be determined in the subject to be diagnosed or treated, determined in samples of the recited subjects having the desired disease or response or being healthy. Preferably, the sample is the same kind of sample as the sample of the person to be diagnosed or to be treated, e.g. when the sample of the latter is serum, the control levels are preferably determined in serum samples derived from the control subjects.

Figure 6:
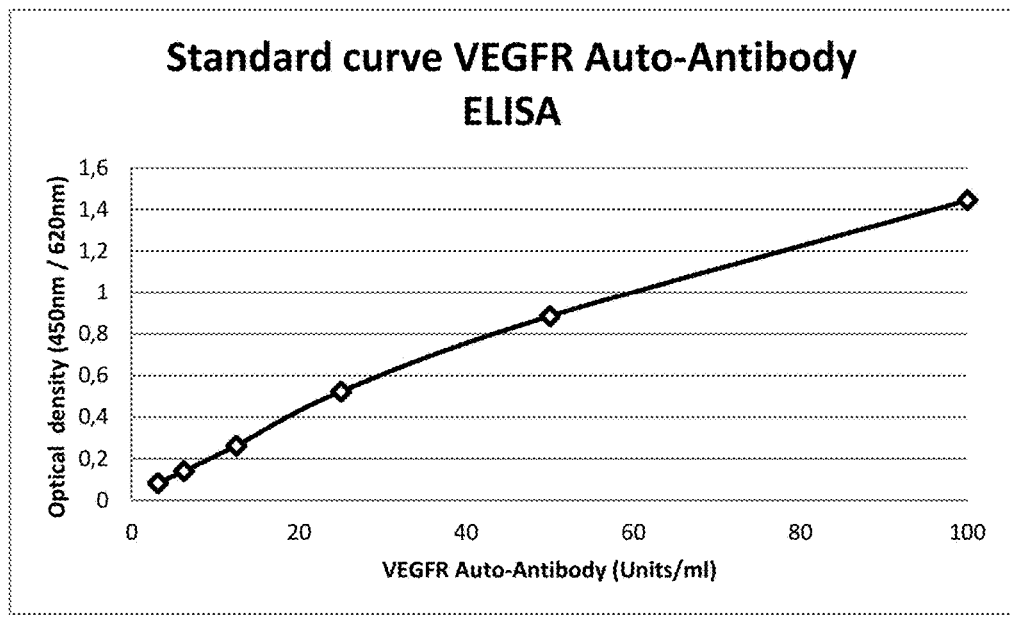
FIG. 6: Standard curve of the VEGFR-Auto-Antibody ELISA

As outlined herein, the levels of VEGFR antibodies in samples of the patient to be diagnosed and treated or to be treated are compared with the control groups as defined herein. However, in one embodiment the levels are compared to fixed values, i.e. thresholds under or over which a certain diagnosis, or prognosis of response is given. To this end, unit-standards may be applied. The present inventors set out such standard for the VEGFR using serum samples from systemic sclerosis patients. Systemic sclerosis patients are known to have high levels of autoimmune antibodies in general. Hence, the inventors took a serum sample of a systemic sclerosis patient. However, it will be acknowledged by the skilled person that also other samples may be taken to set a different standard, e.g. samples of healthy subjects, samples of cancer patients. Nevertheless the principle of generating a standard (units) is the same in any case and are exemplified herein using serum samples of systemic sclerosis patients. In the context of the present invention "units/ml", unless specified otherwise, refers to the concentration of antibodies standardised as exemplified herein. Hence, in one embodiment of the present invention 100 units/ml refers to a dilution of 1:100 of a serum sample of systemic sclerosis patients. The serum sample may be derived from a single patient or of a cohort of a plurality of patients, e.g. a cohort of 200 patients suffering from systemic sclerosis. The present inventors found that the concentration of VEGFR antibodies in samples of systemic sclerosis do not differ by more than about 10%, showing such standard being reproducible. In one preferred embodiment the standard for the concentrations of the autoimmune antibodies is generated in the following way: a serum sample of a systemic sclerosis patient (or a larger cohort) is diluted (a) 1:100 for standard point 100 Units/ml, (b) 1:200 for standard point 50 Units/ml, (c) 1:400 for standard point 25 Units/ml, (d) 1:800 for standard point 12.5 Units/ml, (e) 1:1600 for standard point 6.25 Units/ml and (f) 1:3200 for standard point 3.13 Units/ml. These standards are then used for the immunoassay chosen, e.g. ELISA, and then correlated with the respective read-out value, e.g. for ELISA optical density at 450 nm/optical density at 620 nm. A typical standard curve of a VEGFR auto-antibody ELISA is shown in FIG. 6. Nevertheless, the skilled person will readily understand that it may also be possible to standardize the levels of VEGFR-autoantibodies using different samples, e.g. samples of healthy subjects or cancer patients.

"equal" level in context with the present invention means that the levels differ by not more than ±10%, preferably by not more than ±5%, more preferably by not more than ±2%. "Decreased" or "increased" level in the context of the present invention mean that the levels differ by more than 10%, preferably by more than 15%, preferably more than 20%. In terms of ratios, equal preferably relates to ratios between 0.9 fold to 1.1 fold, preferably between 0.95 fold to 1.05 fold, more preferably 0.98 fold to 1.02 fold.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

In the method of the present invention, the anti-VEGFR antibody is preferably detected in an immunoassay. Suitable immunoassays may be selected from the group of immunoprecipitation, enzyme immunoassay (EIA)), enzyme-linked immunosorbenassys (ELISA), radioimmunoassay (RIA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay such as a luciferase assay. Preferably herein the immunoassay is an enzyme linked immunosorbent assay (ELISA).

The immunoassays can be homogeneous or heterogeneous assays, competitive and non-competitive assays. In a particularly preferred embodiment, the assay is in the form of a sandwich assay, which is a non-competitive immunoassay, wherein the anti-VEGFR antibody (i.e. the "analyte") to be detected and/or quantified is allowed to bind to an immobilized VEGFR protein or immunogenic peptide fragment thereof and to a secondary antibody. The VEGFR or fragment thereof (i.e. a peptide), may e.g., be bound to a solid phase, e.g. a bead, a surface of a well or other container, a chip or a strip, and the secondary antibody is an antibody which is labeled, e.g. with a dye, with a radioisotope, or a reactive or catalytically active moiety such as a peroxidase, e.g. horseradish peroxidase. The amount of labeled antibody bound to the analyte is then measured by an appropriate method. The general composition and procedures involved with "sandwich assays" are well-established and known to the skilled person (*The Immunoassay Handbook, Ed. David Wild, Elsevier LTD, Oxford; 3rd ed*. (May 2005), ISBN-13: 978-0080445267; Hultschig C et al., *Curr Opin Chem Biol*. 2006 February; 10(1):4-10. PMID: 16376134, incorporated herein by reference). Sandwich immunoassays can for example be designed as one-step assays or as two-step assays.

The detectable label may for example be based on fluorescence or chemiluminescence. The labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, *Encyclopedia of chemical technology*, 4$^{th}$ *ed*., executive editor, J L Kroschwitz; editor, M Howe-Grant, John Wiley & Sons, 1993, vol. 15, p. 518-562, incorporated herein by reference, including citations on pages 551-562. Preferred chemiluminescent dyes are acridiniumesters.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive the immunoassay is. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

An "immunogenic peptide" or "antigenic peptide" as used herein is a portion of a VEGFR protein that is recognized (i.e., specifically bound) by the anti-VEGFR antibody. Such immunogenic peptides generally comprise at least 5 amino acid residues, more preferably at least 10, and still more preferably at least 20 amino acid residues of VEGFR. However, they may also comprise at least 30, 40, 50, 60, 70, 80, 90, 100, 110, 120, 130, 140 or 150 amino acid residues.

For the purposes of the immunoassays and diagnostic methods of the invention VEGFR by expression in cells, preferably eukaryotic cells or in cell free, preferably eukaryotic cell free systems. Hence, in the assays and methods of the invention VEGFR may be present in its natural cellular environment and can be used together with the material associated with the receptor in its natural state as well as in isolated form. Suitable expression systems include Chinese hamster ovary (CHO) cells overexpressing the human VEGFR. Hence, cell extracts (particularly extracts from CHO cells overexpressing the human VEGFR) can be used to detect anti-VEGFR antibodies. Based on the weight of the whole receptor in the preparation (e.g. the "extract") to be used according to the invention, the isolated receptor should account for at least 0.5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the factor.

In particular, the method of the present invention comprises the steps of
(a) contacting the sample with VEGFR or an antigenic peptide fragment under conditions allowing for the formation of a complex between anti-VEGFR antibodies with VEGFR or the antigenic peptide fragment thereof,
(b) detecting the complex.

Hence, the invention relates to an immunoassay method for detecting an anti-VEGFR antibody in a sample from a subject, comprising the steps of
(a) contacting the sample suspected of comprising an anti-VEGFR antibody with VEGFR or an antigenic peptide fragment thereof under conditions allowing for the formation of a complex between the anti-VEGFR antibody with VEGFR or the antigenic peptide fragment thereof,
(b) detecting the complex.

The VEGFR or the antigenic peptide fragment thereof may preferably be immobilized on a surface. The complex may for example be detected using a secondary antibody against the Fc portion of the anti-VEGFR antibody. When the anti-VEGFR antibody is an IgG-antibody, the secondary antibody may be an anti-IgG antibody. In a particular embodiment, the subject is a human and
(i) the anti-VEGFR antibody is a IgG1-antibody and the secondary antibody is an anti-human-IgG1 antibody; or (ii) the anti-VEGFR antibody is a IgG2-antibody and the secondary antibody is an anti-human-IgG2 antibody; or
(iii) the anti-VEGFR antibody is a IgG3-antibody and the secondary antibody is an anti-human-IgG3 antibody; or
(iv) the anti-VEGFR antibody is a IgG4-antibody and the secondary antibody is an anti-human-IgG4 antibody.

The secondary antibody may for example be labeled with a detectable marker, e.g. a peroxidase.

Furthermore, in the methods of the present invention further parameters of the subject may be considered as well for diagnosis, differential diagnosis, prognosis of response etc. Such parameters in a multivariate model may include gender, age, histological evaluation, Figo or histopathological staging, grading of the tumor and other markers. Dependent variables for determining survival may also be time till death, time till first relapse, time till death or first relapse (shorter interval if both events occurred). A Cox-Proportional-Hazard regression predicts the dependent variable based on one or more independent variables. These predictors can either be measures (as e.g. level of a biomarker) or categorical data (as e.g. response to a previous treatment). The skilled person is aware of the fact that diagnostic markers only give a certain degree of sensitivity and specificity, as also outlined herein. He knows that different further parameters might be considered in order to increase both. For example, when detecting levels of a marker indicative for epithelial cancer, inter alia ovarian cancer, the skilled person would not diagnose ovarian cancer in a male human subject. Nevertheless, the present invention provides a new and superior marker for diagnosis, prognosis of cancer, particularly for ovarian cancer. In the context of the methods of the invention and particularly the immunoassays of the invention, the presence of one or more further diagnostic markers for ovarian cancer is detected in the sample. For example, in a diagnostic method of the present invention levels of CA125, Human Epidymis Protein 4 (HE4) and/or Mesothelin are detected in addition.

The invention also relates to the use of VEGFR or an antigenic peptide fragment thereof, preferably as set out herein above, for the diagnosis of cancer, preferably for the diagnosis of an VEGF or VEGFR associated cancer, more preferably for the diagnosis of a cancer selected from the group consisting of ovarian cancer, lung cancer, renal cancer, colon cancer, and colorectal cancer.

In the context of the present invention, the levels of the anti-VEGFR antibodies a may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having ovarian cancer) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Suitable threshold levels for the stratification of subjects into different groups (categories) have to be determined for each particular combination of VEGFR-antibodies, disease and/or medication. This can e.g. be done by grouping a reference population of patients according to their level of VEGFR-antibodies into certain quantiles, e.g. quartiles, quintiles or even according to suitable percentiles. For each of the quantiles or groups above and below certain percentiles, hazard ratios can be calculated comparing the risk for an adverse outcome, i.e. an "cancer" or a "non response", e.g. in terms of survival rate/mortality, between those patients who have received a certain medication and those who did not, or in terms of presence and absence of cancer in patients. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g. +/−0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

In some cases presence of cancer, relapse and/or mortality upon treatment with an angiogenesis inhibitor will affect patients with high levels (e.g. in the fifth quintile) of VEGFR-antibodies, while in other cases only patients with low levels of VEGFR-antibodies will be affected (e.g. in the first quintile). However, with the above explanations, a skilled person is able to identify those groups of patients having cancer, those groups that do respond to a medication and those groups that do not respond to the medication. Exemplarily, some combinations of hormones and medications are listed for several diseases in the appended examples. In another embodiment of the invention, the diagnosis, risk for relapse of cancer and/or mortality and/or outcome for a patient are determined by relating the patient's individual level of marker peptide to certain percentiles (e.g. 97.5th percentile) of a healthy population.

Kaplan-Meier estimators may be used for the assessment or prediction of the outcome or risk (e.g. diagnosis, relapse, progression or morbidity) of a patient.

The invention also pertains to a research and/or diagnostic kit for the diagnosis of cancer, e.g. ovarian cancer, or for the prediction of risk stratification for relapse of cancer and/or mortality in a patient, wherein the kit comprises VEGFR or an antigenic peptide fragment thereof. The kit may further comprise an antibody directed to the Fc portion of the anti-VEGFR antibody to be detected, i.e. an anti-human IgG antibody.

Such kits can comprise a carrier, package or container that is compartmentalized to receive one or more containers such as vials, tubes, and the like, each of the container(s) comprising one of the separate elements to be used in the method. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described herein. Directions and or other information can also be included on an insert which is included with the kit.

The term "drug" in connection with the present invention is to be understood as any substance, pharmaceutical composition or the like which are intended for the treatment of cancer, preferably an VEGFR or VEGF associated cancer as outlined herein, particularly preferred ovarian cancer. Different drugs are known. Preferred drugs are angiogenesis inhibitors, e.g. VEGFR or VEGF inhibitors. Drugs used in the treatment of cancer include therapeutic antibodies such as bevacizumab (sold as Avastin® by Roche), aflibercept (Zaltrap), cetuximab, zalutumumab, nimotuzumab, and matuzumab, and are preferably selected from this group. In a preferred embodiment the drug used for the treatment of cancer are drugs directed against angiogenesis, i.e. angiogenesis inhibitors. Angiogenesis is a physiological process through which new blood vessels form from pre-existing vessels and plays a fundamental role in the transition of tumors from a benign state to a malignant one. Angiogenesis inhibitors are therefore well known drugs for the treatment of cancer and are preferred in the present invention. They include and are preferably selected from the group consisting of bevacizumab, aflibercept (Zaltrap), cetuximab, zalutumumab, nimotuzumab, and matuzumab. Bevacizumab (Trade name Avastin®, Roche) is a particularly preferred drug according to the present invention and is slows the growth of new blood vessels. It is licensed to treat various cancers, including colorectal cancer, colon cancer, lung cancer, breast cancer, glioblastoma, kidney (renal) renal and ovarian cancer. In a preferred embodiment the angiogenesis inhibitor is bevacizumab. Furthermore, "drug" also refers to chemotherapeutic agents, preferably platinum analogues used for treating cancer. Such platinum analogues are known by the skilled person and are preferably selected form the group consisting of cisplatin, carboplatin, oxaliplatin, satraplatin, and triplatin-tetranitrate, preferably cisplatin or carboplatin.

Also encompassed by the invention is a method of treating cancer in a subject, comprising determining the level of antibodies against VEGFR in a sample from the subject, wherein when the level of anti-VEGFR antibodies in a sample from the subject is above a level determined as the control level for no-response to the treatment with a method according to the present invention as disclosed herein above. Preferably the invention encompasses a method of treating ovarian cancer in a subject, comprising determining the level of antibodies against VEGFR in a sample from the subject, wherein when the level of anti-VEGFR antibodies in a sample from the subject is above 6 units/ml, a drug as defined herein is administered to the subject, preferably above 9, more preferably above 12, further preferred above 15 unit/ml. Drugs used in the treatment of cancer include therapeutic antibodies, such as bevacizumab.

The invention, thus, also relates a drug for use in the treatment of cancer in a subject, wherein the drug is administered to the subject when a level of anti-VEGFR antibodies in a sample from the subject above a level determined as the control level for non-response to the treatment is determined, preferably using a method according to the present invention. The skilled person will acknowledge that the embodiments of the method for predicting whether a subject to be treated for cancer with a drug will respond to said treatment as outlined herein, also apply to the drug for use in the treatment. He will acknowledge that the drug is for use in the treatment of cancer in a subject, wherein the subject is predicted to respond to the treatment, i.e. if the VEGF levels determined in a method according to the present invention are indicative for the response of the subject to the treatment. Particularly the invention relates to a drug for use in the treatment of cancer in a subject, wherein the drug is administered to the subject when the level anti-VEGFR antibodies in a sample from the subject is above 6 units/ml, preferably above 9, more preferably above 12, further preferred above 15 unit/ml. In a preferred embodiment the drug is for use in the treatment of an VEGF or VEGFR associated cancer, preferably a solid organ cancer, squamous cell carcinoma, or metastatic cancer, preferably selected from the group consisting of colorectal cancer, colon lung cancer, breast cancer, glioblastoma, kidney (renal) renal and ovarian cancer. The drug is preferably bevacizumamb. In a further preferred embodiment the drug is an angiogenesis inhibitor, preferably for use in the treatment of ovarian cancer, more preferably a monoclonal antibody binding VEGF or VEGFR, preferably binding the extracellular part of VEGFR. The invention, thus, also relates to Bevacizumab for use in the treatment of ovarian cancer in a subject, wherein bevacizumab is administered to the subject when the level anti-VEGFR antibodies in a sample from the subject is above 6 units/ml, preferably above 9, more preferably above 12, further preferred above 15 unit/ml.

The invention furthermore relates to a kit for diagnosing cancer as outlined above, or predicting the response of a cancer patient to the treatment for cancer, said kit comprising VEGFR or an antigenic peptide thereof, and means to detect antibodies binding to said VEGFR or peptide thereof. Preferably the kit is designed for a method of the present invention. It will be understood that the embodiments disclosed herein above for VEGFR or an antigenic peptide thereof as set out herein above also apply to the kit. The kit is designed to detect autoimmune antibodies in samples of subject and hence comprises means to detect such antibodies, particularly antibodies binding to said VEGFR or peptide thereof. Such means are outlined herein above, e.g. for immunoassays. The embodiments set out for the immunoassays apply also to the kit of the invention. The kits of the present invention are meant for the detection of autoimmune antibodies. Hence, in one embodiment they comprise means for the preparation of blood, e.g. for gaining serum thereof. Furthermore, the kit may comprise control composition and/or standards. The control composition preferably comprises VEGFR antibodies as positive control. Furthermore, the kit may comprise one or a plurality of standard compositions. A standard composition comprises VEGFR antibodies at a defined concentration. As outlined herein, determination of concentration of autoimmune-antibodies may be performed using standard curves. These curves set out which concentration of antibodies in a sample or solution corresponds to what read-out value of the assay used, e.g. optical density or proportion of optical density at different wavelengths (e.g. 450 nm/620 nm). To this end the kits of the present invention may comprise one or more standard compositions having a defined concentration of VEGFR antibodies, preferably of the kind to be detected in the method. A standard composition of the kits according to the present invention comprise VEGFR antibodies at concentrations selected from the group consisting of 100 units/ml, 50 units/ml, 25 units/ml, 12.5 units/ml, 6.25 units/ml, and 3.13 units/ml. In one embodiment the kit comprises six standard compositions with the recited concentration. In another embodiment the kit comprises one standard composition with the highest concentration of the standard curve, e.g. 200 units/ml or 100 units/ml. The other concentrations may be produced at the side of the end user by further dilutions, e.g. in PBS. A dilution buffer may therefore also be comprised in the kits according to the invention.

It will be readily understood that the embodiments outlined above shall apply to the invention as a whole and not be limited to a specific method, unless stated otherwise. It will for example be understood the embodiments for the type of cancer shall be applied to every method, kit or the like disclosed herein. The invention is further illustrated by the following non-limiting examples and figures.

```
SEQ ID NO: 1:
Amino acid sequence of sVEGFR-1 (sFlc1) [SEQ ID NO: 1]:
    1   MVSYWDTGVL  LCALLSCLLL  TGSSSGSKLK  DPELSLKGTQ  HIMQAGQTLH

51   LQCRGEAAHK  WSLPEMVSKE  SERLSITKSA  CGRNGKQFCS  TLTLNTAQAN

101   HTGFYSCKYL  AVPTSKKKET  ESAIYIFISD  TGRPFVEMYS  EIPEIIHMTE

151   GRELVIPCRV  TSPNITVTLK  KFPLDTLIPD  GKRIIWDSRK  GFIISNATYK

201   EIGLLTCEAT  VNGHLYKTNY  LTHRQTNTII  DVQISTPRPV  KLLRGHTLVL

251   NCTATTPLNT  RVQMTWSYPD  EKNKRASVRR  RIDQSNSHAN  IFYSVLTIDK

301   MQNKDKGLYT  CRVRSGPSFK  SVNTSVHIYD  KAFITVKHRK  QQVLETVAGK

351   RSYRLSMKVK  AFPSPEVVWL  KDGLPATEKS  ARYLTRGYSL  IIKDVTEEDA

401   GNYTILLSIK  QSNVFKNLTA  TLIVNVKPQI  YEKAVSSFPD  PALYPLGSRQ

451   ILTCTAYGIP  QPTIKWFWHP  CNHNHSEARC  DFCSNNEESF  ILDADSNMGN

501   RIESITQRMA  IIEGKNKMAS  TLVVADSRIS  GIYICIASNK  VGTVGRNISF
```

```
bb1   YITDVPNGFH VNLEKMPTEG EDLKLSCTVN KFLYRDVTWI LLRTVNNRTM

601   HYSISKQKMA ITKEHSITLN LTIMNVSLQD SGTYACRARN VYTGEEILQK

651   KEITIRGEHC NKKAVFSRIS KFKSTRNDCT TQSNVKH

SEQ ID NO: 2
Amino acid sequence of mbVEGFR-1 (isoform 1) [SEQ ID NO: 2]:
  1   MVSYWDTGVL LCALLSCLLL TGSSSGSKLK DPELSLKGTQ HIMQAGQTLH

51   LQCRGEAAHK WSLPEMVSKE SERLSITKSA CGRNGKQFCS TLTLNTAQAN

101   HTGFYSCKYL AVPTSKKKET ESAIYIFISD TGRPFVEMYS EIPEIIHMTE

151   GRELVIPCRV TSPNITVTLK KFPLDTLIPD GKRIIWDSRK GFIISNATYK

201   EIGLLTCEAT VNGHLYKTNY LTHRQTNTII DVQISTPRPV KLLRGHTLVL

251   NCTATTPLNT RVQMTWSYPD EKNKRASVRR RIDQSNSHAN IFYSVLTIDK

301   MQNKDKGLYT CRVRSGPSFK SVNTSVHIYD KAFITVKHRK QQVLETVAGK

351   RSYRLSMKVK AFPSPEVVWL KDGLPATEKS ARYLTRGYSL IIKDVTEEDA

401   GNYTILLSIK QSNVFKNLTA TLIVNVKPQI YEKAVSSFPD PALYPLGSRQ

451   ILTCTAYGIP QPTIKWFWHP CNHNHSEARC DFCSNNEESF ILDADSNMGN

501   RIESITQRMA IIEGKNKMAS TLVVADSRIS GIYICIASNK VGTVGRNISF

551   YITDVPNGFH VNLEKMPTEG EDLKLSCTVN KFLYRDVTWI LLRTVNNRTM

601   HYSISKQKMA ITKEHSITLN LTIMNVSLOD SGTYACRARN VYTGEEILQK

651   KEITIRDQEA PYLLRNLSDH TVAISSSTTL DCHANGVPEP QITWFKNNHK

701   IQQEPGIILG PGSSTLFIER VTEEDEGVYH CKATNOKGSV ESSAYLTVQG

751   TSDKSNLELI TLTCTCVAAT LFWLLLTLFI RKMKRSSSEI KTDYLSIIMD

801   PDEVPLDEQC ERLPYDASKW EFARERLKLG KSLGRGAFGK VVQASAFGIK

851   KSPTCRTVAV KMLKEGATAS EYKALMTELK ILTHIGHHLN VVNLLGACTK

901   QGGPLMVIVE YCKYGNLSNY LKSKRDLFFL NKDAALHMEP KKEKMEPGLE

951   QGKKPRLDSV TSSESFASSG FQEDKSLSDV EEEEDSDGFY KEPITMEDLI

1001  SYSFQVARGM EFLSSRKCIH RDLAARNILL SENNVVKICD FGLARDIYKN

1051  PDYVRKGDTR LPLKWMAPES IFDKIYSTKS DVWSYGVLLW EIFSLGGSPY

1101  PGVQMDEDFC SRLREGMRMR APEYSTPEIY QIMLDCWHRD PKERPRFAEL

1151  VEKLGDLLQA NVQQDGKDYI PINAILTGNS GFTYSTPAFS EDFFKESISA

1201  PKFNSGSSDD VRYVNAFKFM SLERIKTFEE LLPNATSMFD DYQGDSSTLL

1251  ASPMLKRFTW TDSKPKASLK IDLRVTSKSK ESGLSDVSRP SFCHSSCGHV

1301  SEGKRRFTYD HAELERKIAC CSPPPDYNSV VLYSTPPI
```

EXAMPLES

Example 1

We measured the anti-VEGFR autoantibody in serum samples using a sandwich ELISA kit (CellTrend GmbH Luckenwalde, Germany). The microtiter 96-well polystyrene plates were coated with human sVEGFR-1 of the sequence of SEQ ID NO:1. To maintain the conformational epitopes of the receptor, 1 mM calcium chloride was added to every buffer. Duplicate samples of a 1:100 serum dilution were incubated at 4° C. for 2 hours. After washing steps, plates were incubated for 60 minutes with a 1:20.000 dilution of horseradish-peroxidase-labeled goat anti-human IgG (Jackson, USA) used for detection. In order to obtain a standard curve, plates were incubated with test sera from an anti-VEGFR autoantibody positive index patient. The ELISA was validated according to the FDA's "Guidance for industry: Bioanalytical method validation".

Figure 7:
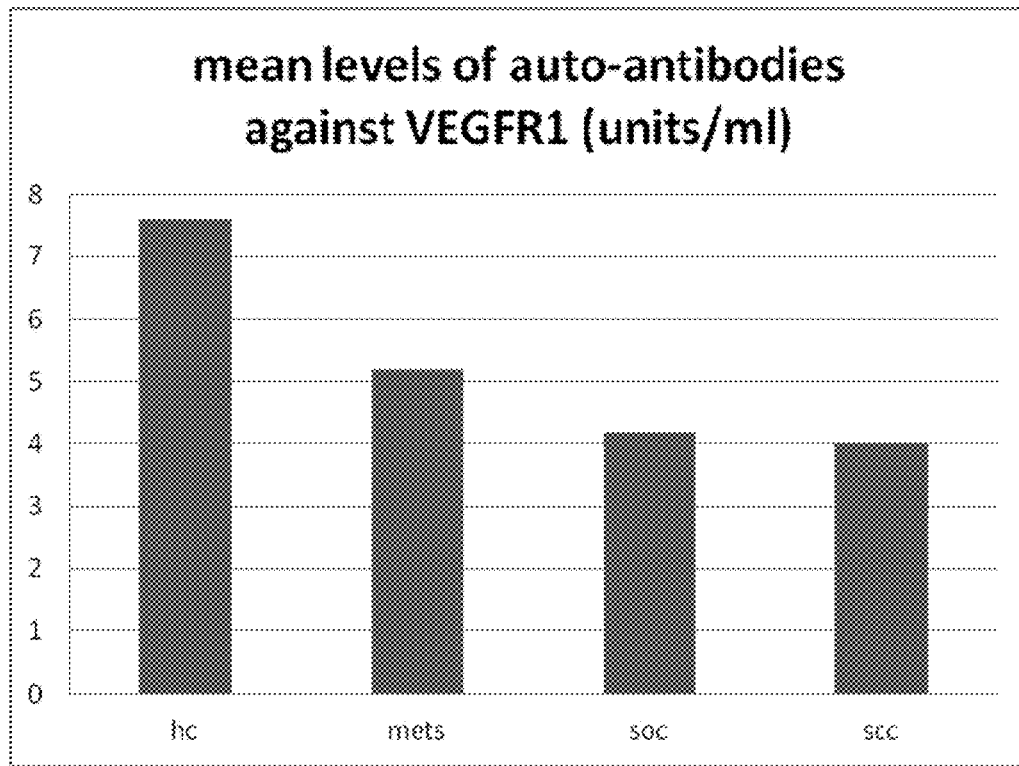
FIG. 7: Comparison of the mean level of anti-VEGFR antibodies (units/ml) in plasma samples of a healthy control group (hc; mean=7.2 units/ml; n=32) to the mean level of anti-VEGFR antibodies in plasma samples patients suffering from metastatic cancer (mets; mean=5.2; n=4), solid organ cancer (soc; mean=4.2 units/ml; n=14), and squamous cell cancer of the skin (scc, mean=4.0; n=25).

VEGF-Receptor-Auto-Antibodies are not available; a serum sample from a patient with a systemic sclerosis is used for the standard curve. A 1:200 dilution of the serum sample is defined as 50 Units VEGFR-Receptor-Antibodies. A 1:100 dilution of a healthy donor served as a positive control (range 7.0-15.0 Units/ml). To set a standard for the concentrations of the autoimmune antibodies, a standard curve was generated. In detail, a serum sample of systemic sclerosis serum sample was diluted (a) 1:100 for standard point 100 Units/ml, (b) 1:200 for standard point 50 Units/ml, (c) 1:400 for standard point 25 Units/ml, (d) 1:800 for standard point 12.5 Units/ml, (e) 1:1600 for standard point 6.25 Units/ml and (f) 1:3200 for standard point 3.13 Units/ml. Then the optical density was determined using the kit and method of example 1. Each standard point was performed in duplicates. Results are shown in FIG. 7.

Example 2

Anti-VEGFR antibody levels in serum samples from 130 healthy donors ("Control") and 201 patients with ovarian cancer ("OvCA") were measured using the kit and method of example 1. The levels were determined in units/mL. FIG. 1 shows the mean values of the natural logarithm of the VEGFR antibody level for OvCA and Control subjects. Patient suffering from ovarian cancer had significantly lower levels ($p<0.0001$) of anti-VEGFR antibodies as compared to healthy controls.

Example 3

Figure 2:
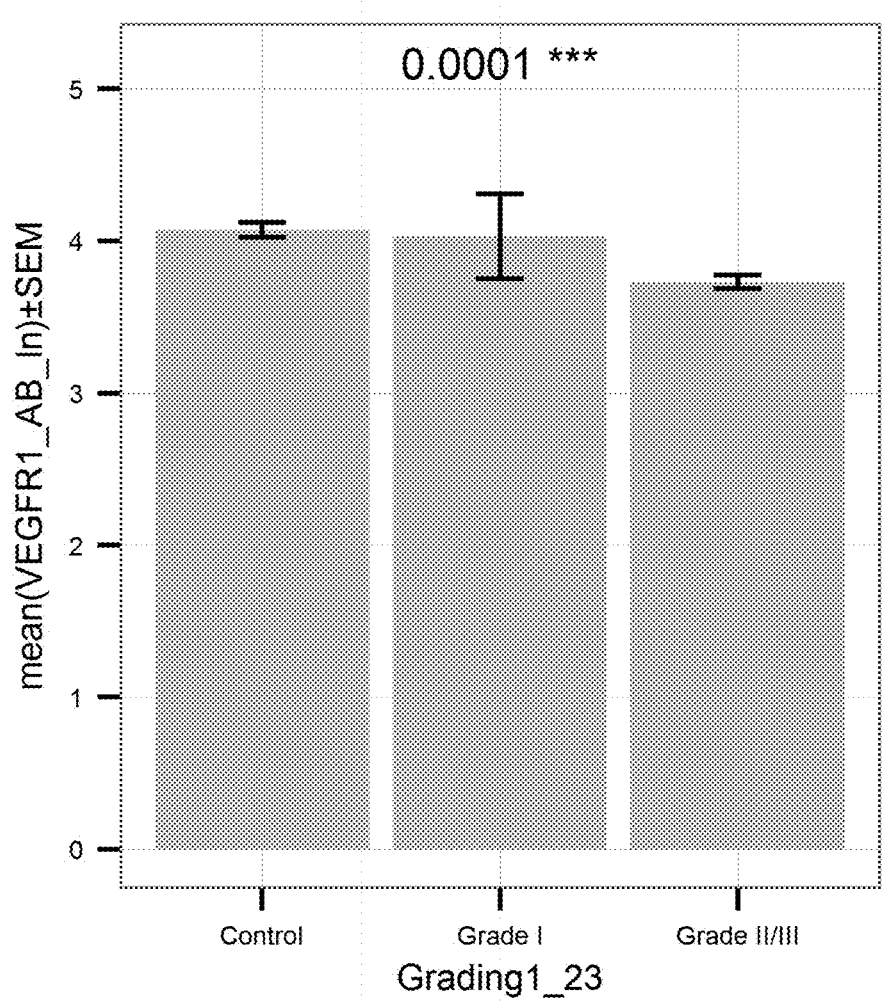
FIG. 2: Comparison of the mean level of anti-VEGFR antibodies (ln of units/ml) in serum samples of ovarian cancer patients suffering from histological Grade I ovarian cancer ("Grade I"; ln of mean=4.031; n=6) to the mean level of anti-VEGFR antibodies in serum samples of a ovarian cancer patients suffering from histological Grade I ovarian cancer ("Grade II/III", ln of mean=3.731 units/ml, n=192) and healthy control subjects ("Control", ln of mean=4.073 units/ml; n=130). The p-value is indicated on top. Bars indicate standard error of mean.

Anti-VEGFR antibody levels in serum samples from 201 healthy donors ("control"; see Example 1), 6 patients with ovarian cancer of histological (differentiation) Grade I ("Grade I") and 192 patients with proven ovarian cancer of histological (differentiation) Grade II or III ("Grade II/III") were measured using the kit and method of example 1. The levels were determined in units/mL. FIG. 2 shows the mean values of the natural logarithm of the VEGFR antibody level for case and control subjects. Patient suffering from ovarian cancer of Grade II or III had significantly lower levels ($p \leq 0.0001$) of anti-VEGFR antibodies as compared to controls.

Example 4

Figure 3:
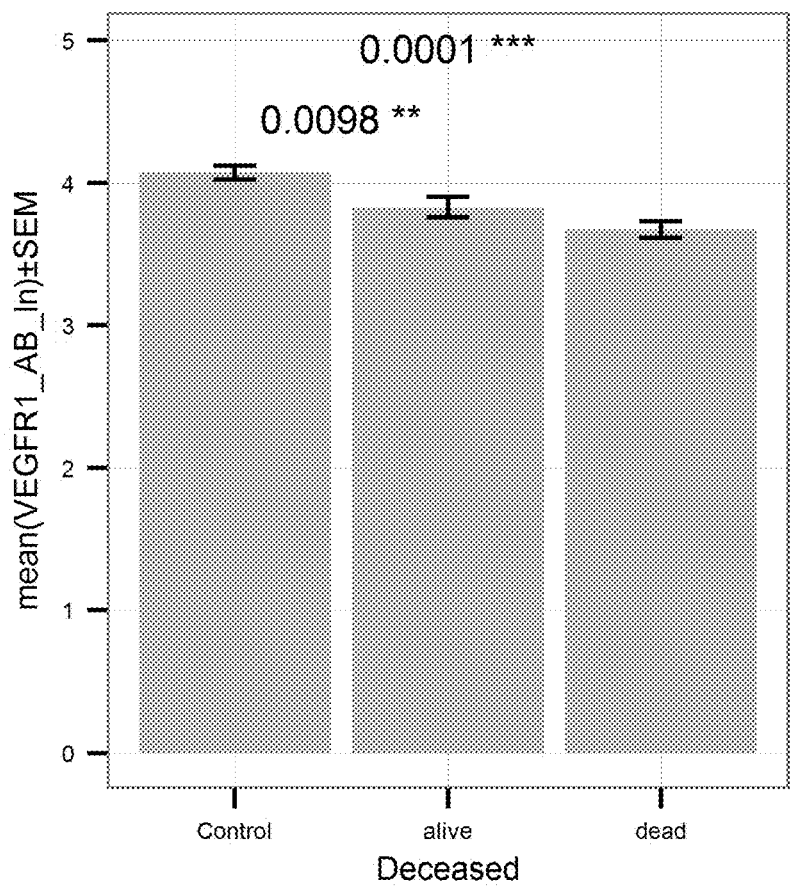
FIG. 3: Comparison of the mean level of anti-VEGFR antibodies (ln of units/ml) in serum samples of ovarian cancer patients who survived ovarian cancer after surgical treatment and chemotherapy with platinum analogue ("alive"; ln of mean=3.83 units/ml; n=71) to the mean level of anti-VEGFR antibodies in serum samples of ovarian cancer patients who died because of their ovarian cancer after surgical treatment and chemotherapy with platinum analogue ("dead"; ln of mean=3.674 units/ml; n=129). The left column gives the healthy control group (ln of mean=4.073 units/ml; n=130). P-values are indicated above. Bars indicate standard error of mean.

Levels of anti-VEGFR antibodies were determined in samples from patients suffering from ovarian cancer taken after surgical removal of the cancer and before onset of treatment with a platinium analogue. The patients were treated with a chemotherapeutic agent (platinium analogue) after surgical removal of ovarian cancer. Results are shown in FIG. 3. Anti-VEGFR antibody levels in samples of patients who survived after the treatment of the cancer were higher than in those who died after said treatment.

Example 5

Serum samples of ovarian cancer patients were taken before treatment with bevacizumab. The treatment was conducted by physicians. The patients were categorized into survivors ("alive") and patients who died after treatment with bevacizumab ("dead"). The levels of anti-VEGFR antibodies were determined as outlined in Example 1. The results are shown in FIG. 4A. Levels of anti-VEGFR antibodies were lower in patients of the "dead" group (mean: 5.53 units/ml) compared to the "survival" group (mean: 24.30 units/ml).

Example 6

Figure 4:
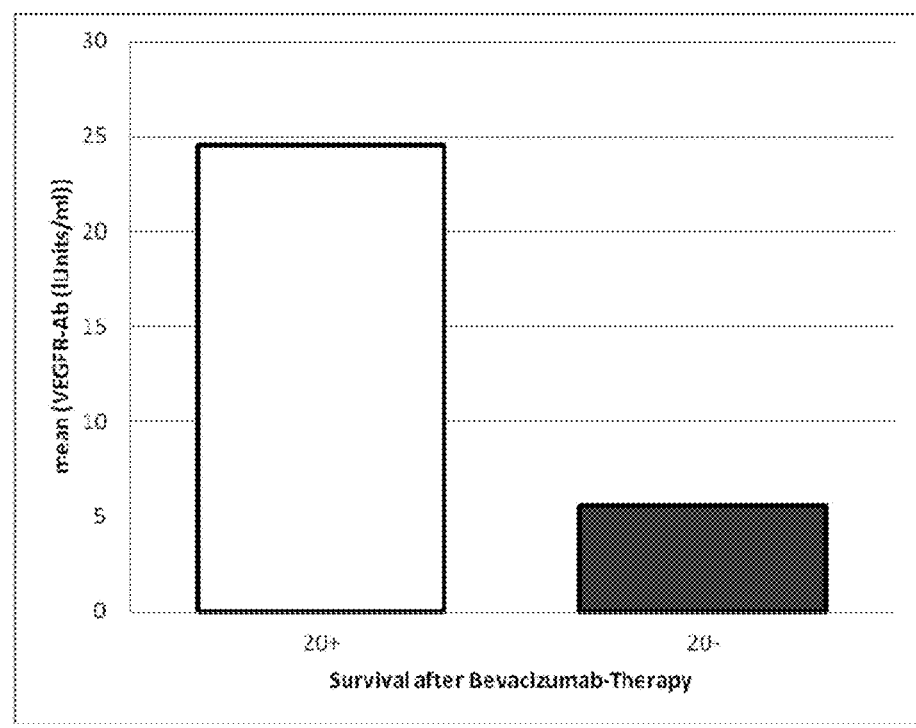
FIG. 4: (A) Prediction of survival after treatment of ovarian cancer with bevacizumab. Samples were taken before onset of treatment. Levels of antibodies directed against VEGFR were measured as outlined in Example 1. The patients were categorized as "survival" longer than 20 months (20+) or "death" within 20 months (20−) and showed a mean VEGFR antibody level of 24.5 units/ml or 5.53 units/ml (mean values), respectively. (B) Prediction of relapse after treatment of ovarian cancer with bevacizumab. Samples were taken before onset of treatment. Levels of antibodies directed against VEGFR were measured as outlined in Example 1. The patients were categorized as "no replapse" within 20 months (20+) or "relapse" within 20 months (20−) and showed a mean VEGFR antibody level of 24.5 units/ml or 5.53 units/ml (mean values), respectively. Bars indicate standard error of mean.
Figure 4:
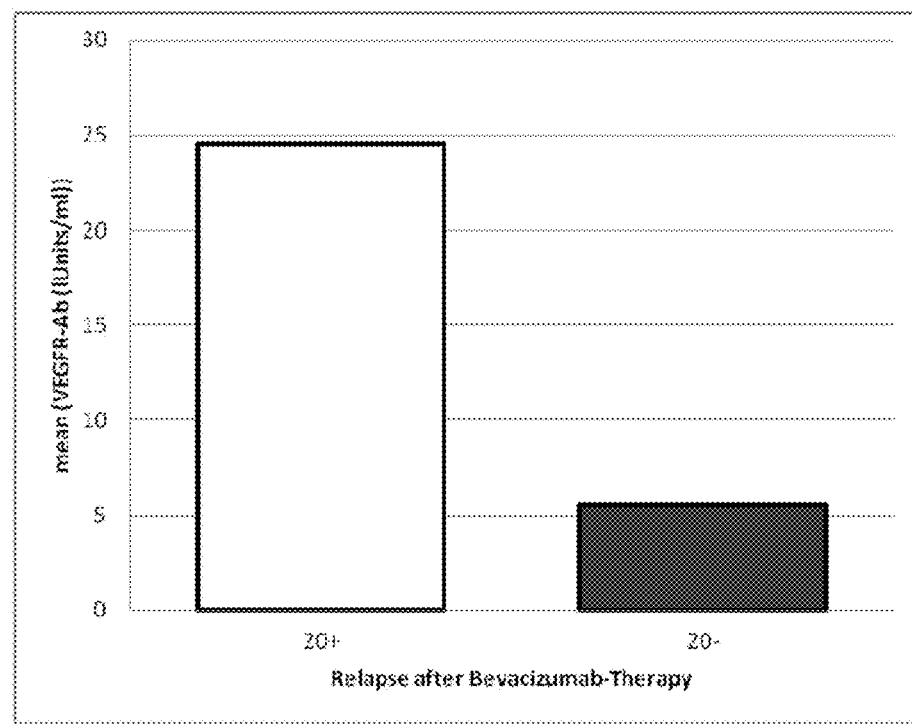

Serum samples of ovarian cancer patients were taken before treatment with bevacizumab. The treatment was conducted by physicians. The patients were categorized into relapse free ("relapse no (20+)") and patients who received a relapse ("relapse yes (20−)"). The levels of anti-VEGFR antibodies were determined as outlined in Example 1. The results are shown in FIG. 4. Levels of anti-VEGFR antibodies were lower in patients of the "relapse yes" group (mean: 5.53 units/ml) compared to the "relapse free" group (mean: 24.50 units/ml).

Example 7

Figure 5:
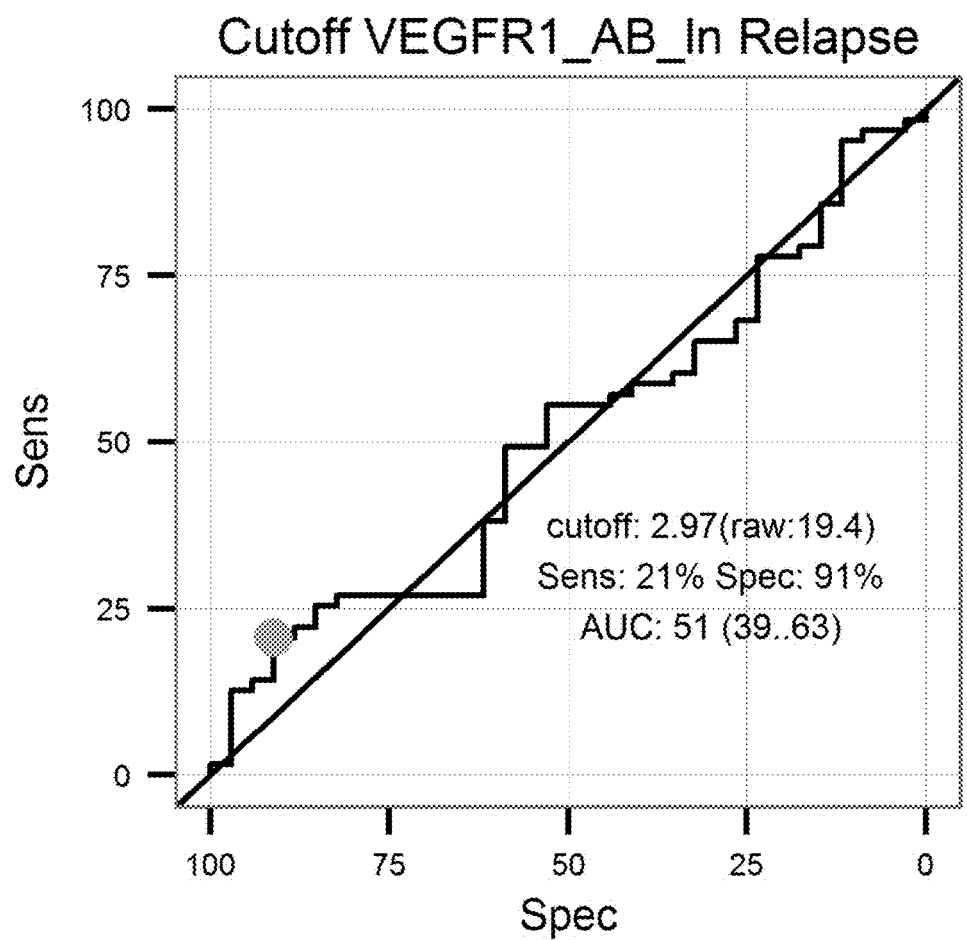
FIG. 5: (A) on top sensitivity of the prediction of relapse of ovarian cancer after surgical treatment and treatment with platinum analogue is plotted against the specificity. Ln of Cutoff value (2.97 units/ml) and AUC is given in the graph. Below the proportion of patients not showing relapse after surgical treatment and treatment with platinum analogue is shown over the time for patients having antibody levels below the ROC-cutoff value (dotted line) and above the ROC-cutoff value (solid line). B: on top sensitivity of the prediction of survival after surgical treatment and treatment with platinum analogue is plotted against the specificity. Ln of Cutoff value (3.5 units/ml) and AUC is given in the graph. Below the proportion of patients surviving after surgical treatment and treatment with platinum analogue is shown over the time for patients having antibody levels below the ROC-cutoff value (dotted line) and above the ROC-cutoff value (solid line). C: on the left sensitivity of the prediction of a combined endpoint (death or relapse of cancer) of ovarian cancer patients after surgical treatment and treatment with platinum analogue is plotted against the specificity. Ln of Cutoff value (3.3 units/ml) and AUC is given in the graph. Below the proportion of patients surviving or not showing relapse of cancer after surgical treatment and treatment with platinum analogue is shown over the time for patients having antibody levels below the ROC-cutoff value (dotted line) and above the ROC-cutoff value (solid line).
Figure 5:
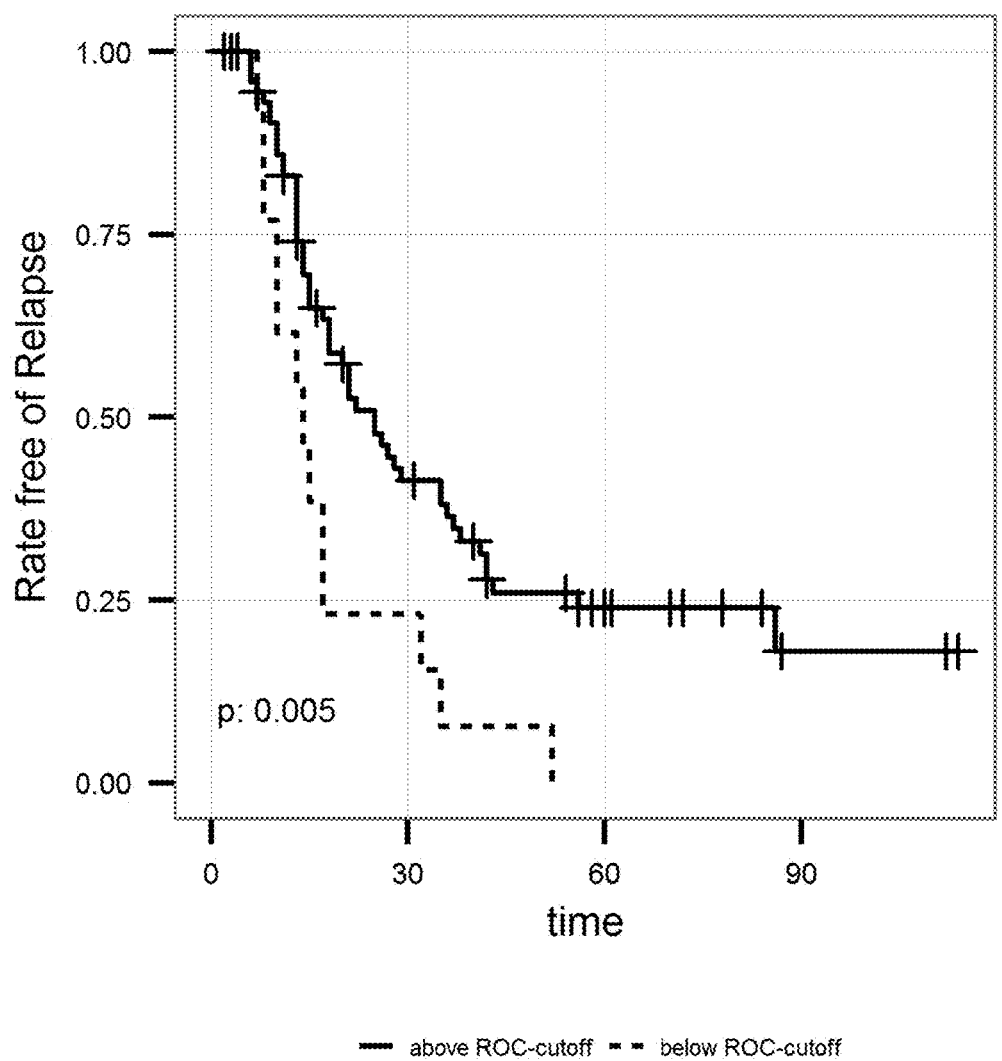
Figure 5:
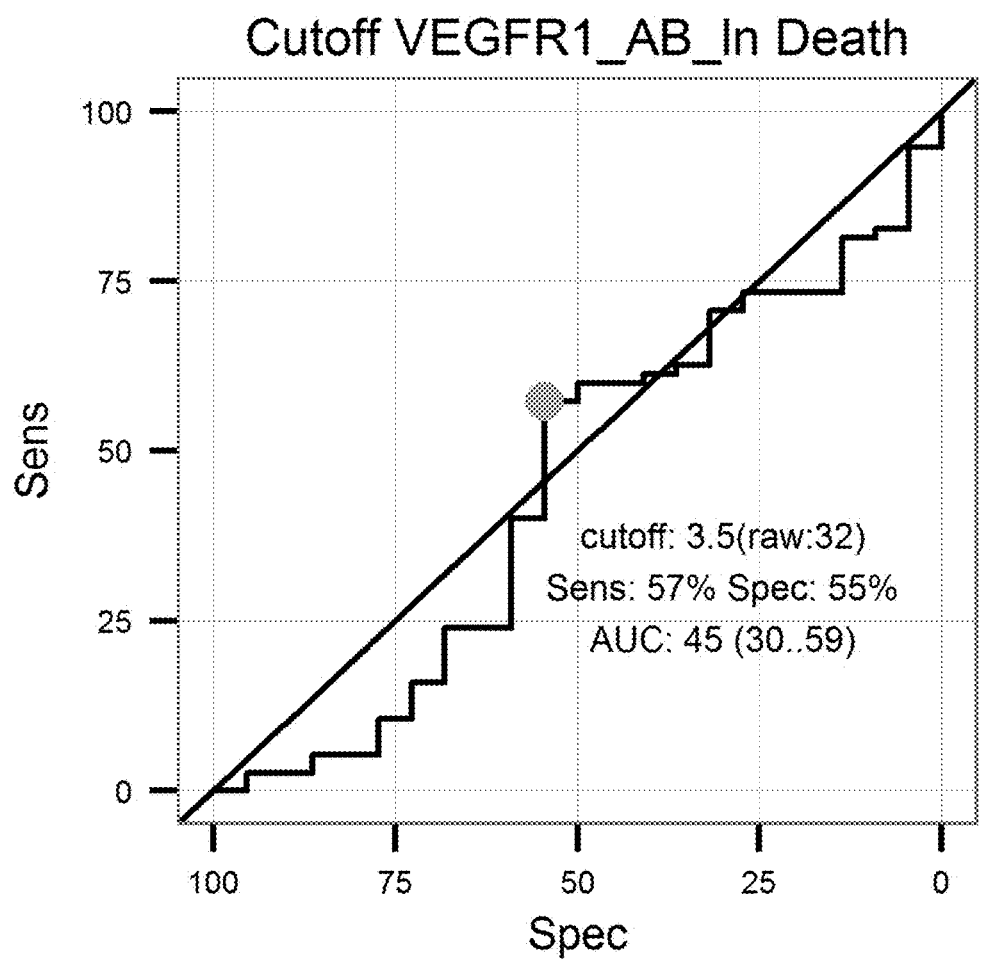
Figure 5:
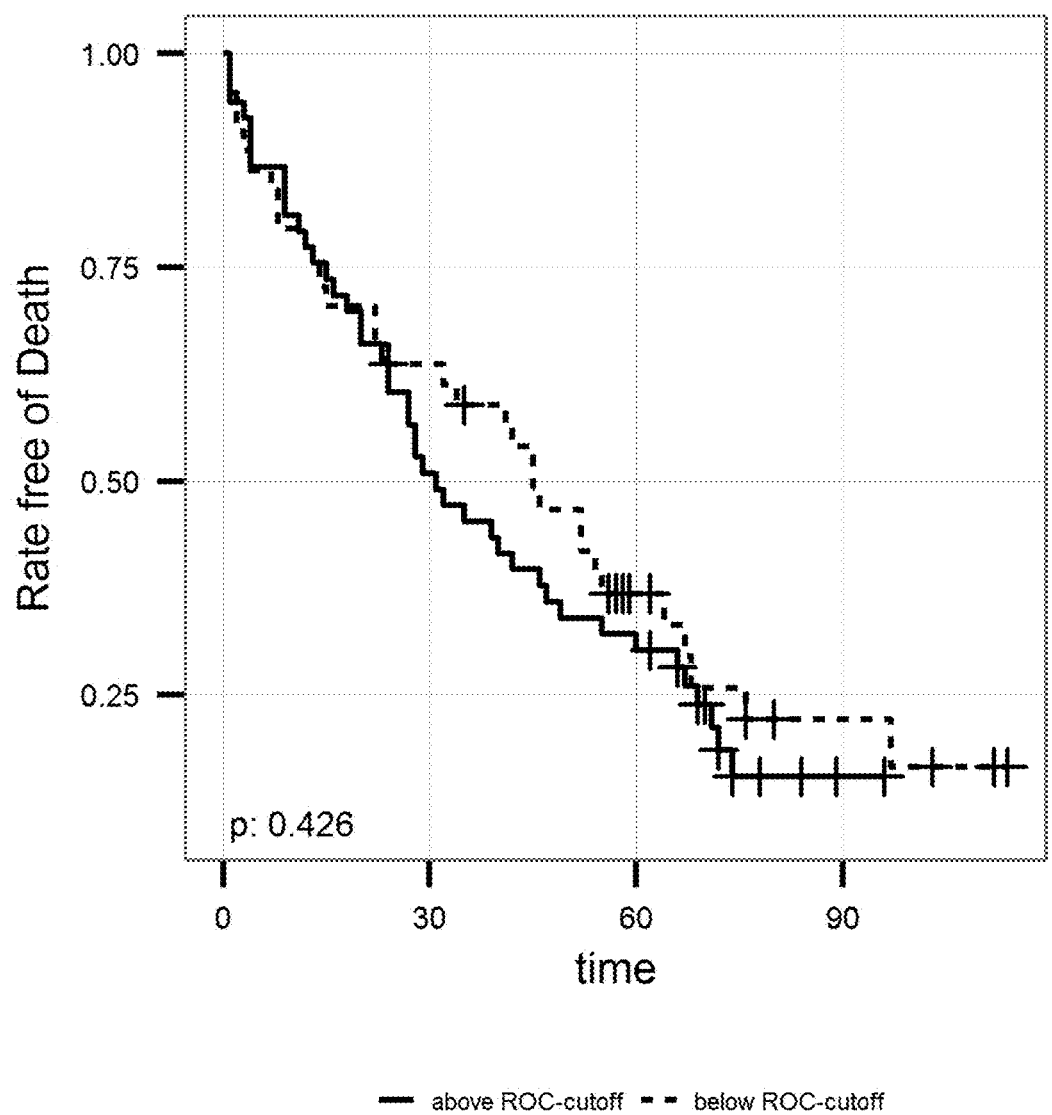
Figure 5:
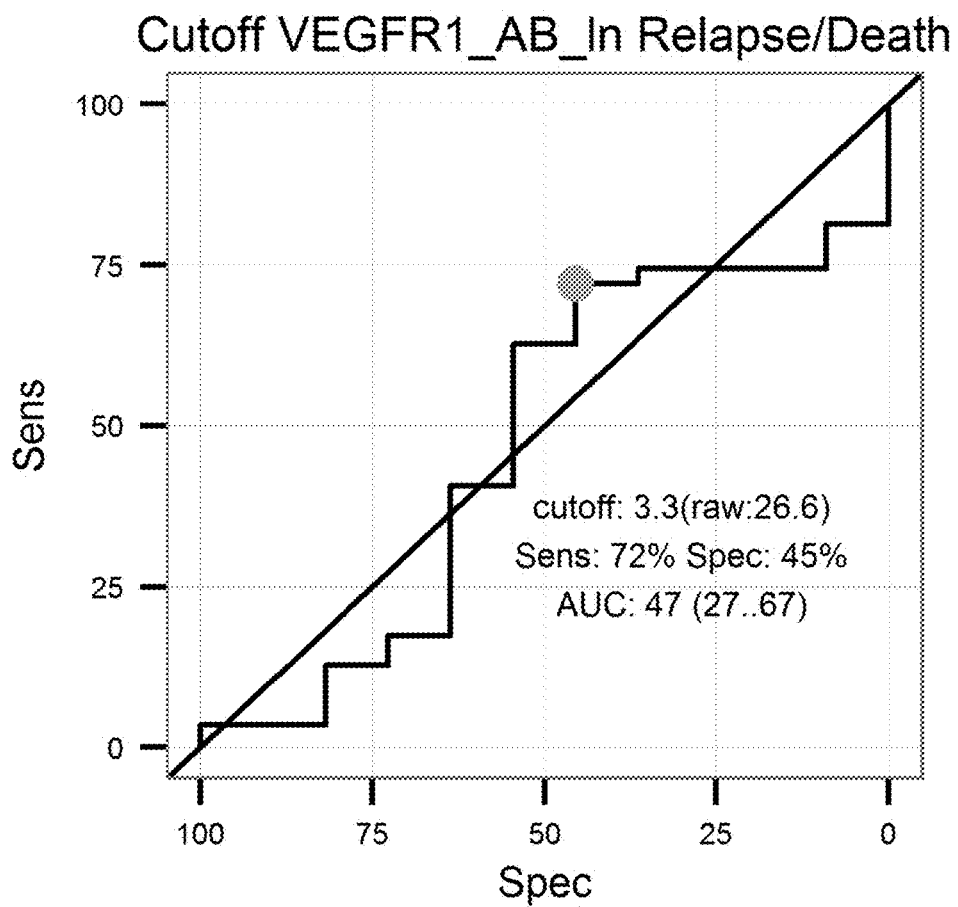
Figure 5:
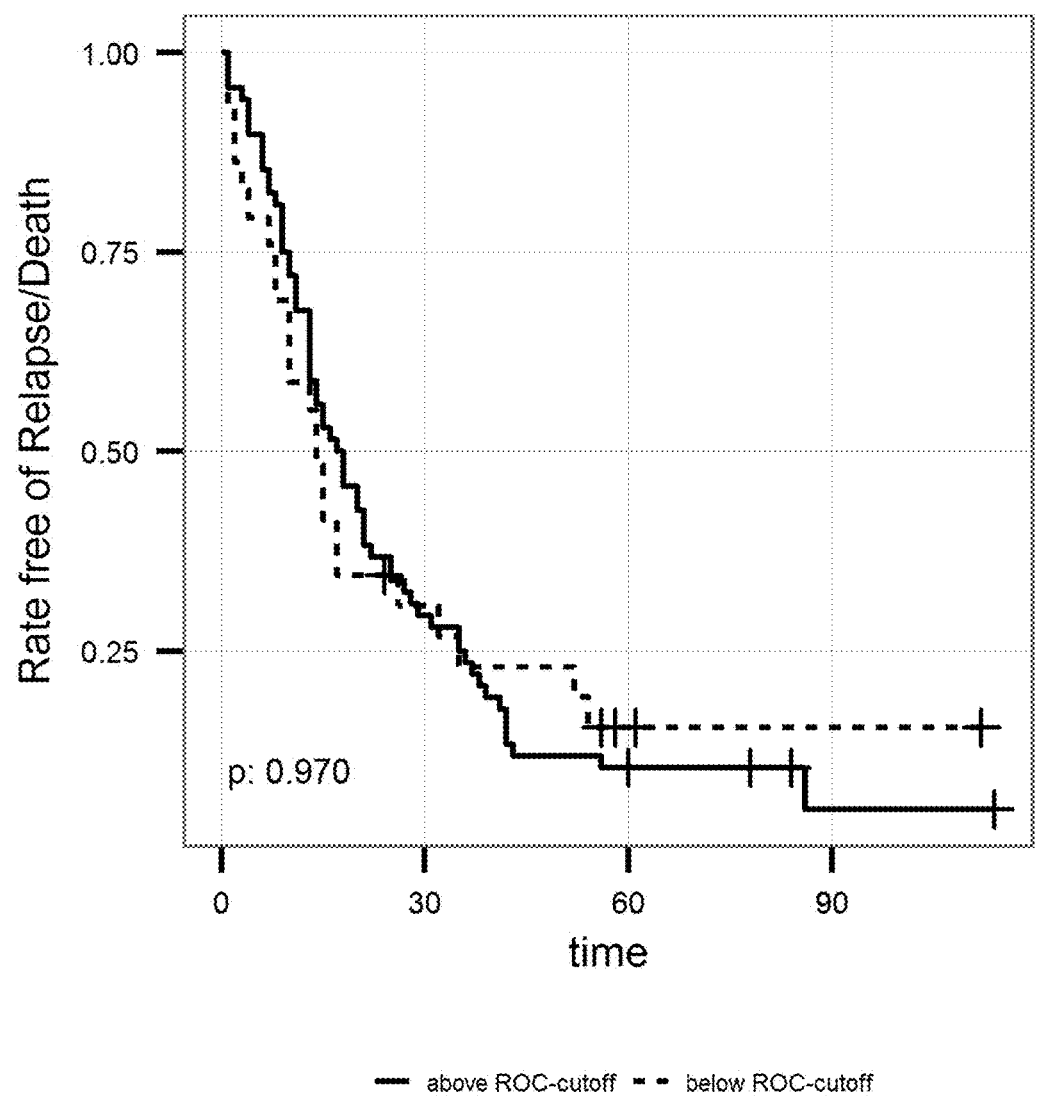

The sensitivity and specificity for levels of anti-VEGFR antibodies as predictor of relapse and/or mortality was calculated using ROC-analysis and Kaplan-Meier estimation. Mortality and relapse were determined after treatment by surgery and platinum analogue. The results for the prediction of relapse are given in FIG. 5A, for the prediction of mortality in FIG. 5B, and for the combined endpoint prediction (relapse or death) in FIG. 5C. The results show that the levels of anti-VEGFR antibodies are a good predictor for relapse or mortality after treatment of cancer patients as endpoint prediction. The specificity and sensitivity of the prediction could be further enhanced when including further factors in a multivariate model. These factors were age, Figo and histology staging.

The p-value for mortality or the combined end-point (mortality or relapse) was $p<0.001$ and $p<0.019$, respectively in the Cox-proportional hazard. For relapse as the single endpoint we observed a significant value. The p-value was 0.01.

Example 8

Anti-VEGFR antibodies levels in plasma samples of a healthy control group, patients suffering from metastatic cancer, patients suffering from solid organ cancer and patients suffering from squamous cell cancer of the skin were measured using the kit and method of Example 1, with the exception that plasma samples were used in a dilution of 1:100 for measurement of samples. The standard curve, however, was the same as in Example 1. The levels were determined in units/mL. FIG. 7 shows the mean values of the VEGFR antibody level. Patient suffering from the tested types of cancers had significantly lower levels of anti-VEGFR antibodies as compared to healthy controls.

Furthermore, ROC analysis for solid organ tumors and squamous cell carcinoma of the skin were performed and showed significant results (AUC 0.66; $p=0.021$).

SUMMARY

The results of the present Examples show that anti-VEGFR antibody levels are significant lower in patients with the tasted cancers, ovarian cancer, metastatic cancer, solid organ cancer and squamous cell cancer of the skin, compared to healthy controls. Levels of anti-VEGFR antibodies in samples of cancer patient are an indicator for the severeness of cancer, e.g. the Grade. This allows differential diagnosis of cancer. Furthermore, the levels are significantly higher in patients in which show no relapse after treatment with Bevacizumab as compared to patients showing relapse or progression of cancer or who died after treatment. Levels of anti-VEGFR antibodies in samples are a well suited predictor for the response to the treatment with an angiogenesis inhibitor. Relapse of cancer or mortality of the patient as endpoints of the treatment can be predicted with a high degree of specificity and sensitivity.

The invention claimed is:

1. A method for treating a vascular endothelial growth factor receptor (VEGFR) or vascular endothelial growth factor (VEGF) associated cancer, comprising
   (i) determining the level of antibodies against VEGFR in a sample from a subject suspected of having such cancer,
   (ii) comparing the determined level in the sample to a control level of VEGFR antibodies derived from subjects without cancer;
   (iii) identifying a subject having a decreased level of said antibodies in the subject's sample as compared to the level of said antibodies in the control, and
   (iv) administering to the subject from step (iii) a drug selected from the group consisting of an angiogenesis inhibitor, an anti-VEGF antibody, and bevacizumab.

2. The method according to claim 1, wherein the subject from step (iii) has a determined level of said antibodies of less than 0.9 fold as compared to the level of said antibodies from subjects without cancer.

3. The method according to claim 1, wherein the anti-VEGFR antibody is detected in an immunoassay.

4. The method according to claim 3, wherein the immunoassay is selected from the group of immunoprecipitation, enzyme immunoassay (EIA), radioimmunoassay (RIA), enzyme-linked immunosorbent assay (ELISA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay a heterogeneous immunoassay, a bioassay and a reporter assay such as a luciferase assay.

5. The method according to claim 1, wherein the sample is plasma or serum.

6. The method according to claim 1, comprising
   (a) contacting the sample with vascular endothelial growth factor receptor (VEGFR) or an antigenic peptide fragment thereof under conditions allowing for the formation of a complex between anti-VEGFR antibodies with VEGFR or a peptide fragment thereof,
   (b) detecting the complex.

7. The method of claim 6, wherein the VEGFR or the peptide fragment thereof is immobilized on a surface.

8. The method according to claim 6, wherein the complex is detected using a secondary antibody against the Fc portion of the anti-VEGFR antibody.

9. The method according to claim 8, wherein the anti-VEGFR antibody is an IgG-antibody and the secondary antibody is an anti-IgG antibody.

10. The method according to claim 9, wherein the secondary antibody is labeled with a detectable marker.

11. The method of claim 1, wherein the presence of one or more further markers for cancer is detected in the sample.

12. A method for treating progression or relapse of a vascular endothelial growth factor receptor (VEGFR) or vascular endothelial growth factor (VEGF) associated cancer in a subject, the method comprising
   (i) determining the level of antibodies against VEGFR in a sample from said subject,
   (ii) comparing the determined level in the sample to either one or both of a first and second VEGFR antibody control level, wherein
      a) the first VEGFR antibody control level is derived from subjects not showing relapse of cancer or mortality after treatment with said drug, and
      b) the second VEGFR antibody control level is derived from subjects showing relapse of cancer or mortality after treatment with said drug, and
   (iii) identifying a subject having a decreased level of said antibodies in the subject's sample as compared to the level of said antibodies in the first VEGFR antibody control and/or having an equal level of said antibodies as compared to the level of said antibodies in the second VEGFR control, and
   (iv) administering to said subject from step (iii) with a drug selected from the group consisting of an angiogenesis inhibitor, an anti-VEGF antibody, and bevacizumab.

13. A method for differential diagnosis and treatment of ovarian cancer comprising
   (i) determining the level of antibodies against vascular endothelial growth factor receptor (VEGFR) in a sample from a subject,
   (ii) comparing the determined level in the sample to either one or both of a first and second VEGFR antibody control level,
      a) wherein the first VEGFR antibody control level is derived from subjects suffering from ovarian cancer classified as Grade II or Grade III ovarian cancer, and
      b) wherein the second VEGFR antibody control level is derived from a subject suffering from ovarian cancer classified as Grade I ovarian cancer,
   (iii) identifying a subject having:
      an increased level of said antibodies in the sample from the subject as compared to the first VEGFR antibody control level; and/or
      an equal level of said antibodies in the sample from the subject as compared to the second VEGFR antibody control level
      as having Grade I ovarian cancer, (iv) identifying a subject having:
a decreased level of said antibodies in the sample from the subject as compared to the second VEGFR antibody control level;
and/or an equal level of said antibodies in the sample from the subject as compared to the first VEGFR antibody control level
as having Grade II or Grade III ovarian cancer, and
(v) administering to the subject from step (iii) or step (iv) a drug selected from the group consisting of an angiogenesis inhibitor, an anti-VEGF antibody, and bevacizumab.

14. The method for differential diagnosis of ovarian cancer according to claim 13, wherein a level of antibodies against VEGFR in the sample from the subject to be diagnosed of less than 0.9 fold as compared to the second VEGFR antibody control level is indicative for Grade II or Grade III ovarian cancer in said subject to be diagnosed, and/or wherein a level of antibodies against VEGFR in the sample from the subject to be diagnosed of more than 1.1 fold as compared to the first VEGFR antibody control level is indicative for Grade I ovarian cancer in said subject to be diagnosed.

* * * * *